(12) United States Patent
Ghandehari et al.

(10) Patent No.: US 10,253,089 B2
(45) Date of Patent: Apr. 9, 2019

(54) MATRIX METALLOPROTEINASE CLEAVABLE PROTEIN POLYMERS FOR CANCER GENE THERAPY

(71) Applicant: The University of Utah Research Foundation, Salt Lake City, UT (US)

(72) Inventors: Hamidreza Ghandehari, Salt Lake City, UT (US); Joseph Cappello, Salt Lake City, UT (US); Jordan Frandsen, Salt Lake City, UT (US); Joshua Gustafson, Seattle, WA (US); Khaled Greish, Salt Lake City, UT (US); Robert Andrew Price, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 14/403,979

(22) PCT Filed: May 30, 2013

(86) PCT No.: PCT/US2013/043487
§ 371 (c)(1),
(2) Date: Nov. 25, 2014

(87) PCT Pub. No.: WO2013/181471
PCT Pub. Date: Dec. 5, 2013

(65) Prior Publication Data
US 2015/0152165 A1    Jun. 4, 2015

Related U.S. Application Data

(60) Provisional application No. 61/689,285, filed on May 30, 2012.

(51) Int. Cl.
*A61K 38/39* (2006.01)
*A61K 47/42* (2017.01)
(Continued)

(52) U.S. Cl.
CPC ............ *C07K 14/78* (2013.01); *A61K 31/522* (2013.01); *A61K 38/39* (2013.01); *A61K 38/45* (2013.01);
(Continued)

(58) Field of Classification Search
CPC ........ A61K 38/16; A61K 38/39; A61K 47/42; A61K 47/48246; A61K 47/48292;
(Continued)

(56) References Cited

U.S. PATENT DOCUMENTS

2006/0009840 A1    1/2006  Hossainy
2010/0143304 A1*   6/2010  Lowenstein ............. C12N 7/00
                                                          424/93.2

(Continued)

FOREIGN PATENT DOCUMENTS

WO    WO2009/158704    12/2009
WO    WO2011/140024    11/2011

OTHER PUBLICATIONS

Mecham et al. Elastin Degradation by Matrix Metalloproteinases. The Journal of Biological Chemistry. Jul. 18, 1997, vol. 272, No. 29, pp. 18071-18076.*
(Continued)

*Primary Examiner* — Jeffrey E. Russel
(74) *Attorney, Agent, or Firm* — Gardner Groff Greenwald & Villanueva, PC

(57) ABSTRACT

A delivery system that includes a recombinantly synthesized protein polymer with protease cleavage sites such as matrix metalloproteinase responsive sequences engineered within the protein polymer. The system may be used to treat cancer, wounds, or pathological conditions in other tissues that express excess protease relative to healthy tissue.

9 Claims, 22 Drawing Sheets

Specification includes a Sequence Listing.

Rationale for SELP-Mediated GDEPT system

(51) Int. Cl.
  A61K 48/00    (2006.01)
  C07K 14/78    (2006.01)
  A61K 47/66    (2017.01)
  A61K 47/65    (2017.01)
  C07K 14/435   (2006.01)
  A61K 31/522   (2006.01)
  A61K 38/45    (2006.01)
  C12N 7/00     (2006.01)
  A61K 47/64    (2017.01)

(52) U.S. Cl.
  CPC .............. *A61K 47/42* (2013.01); *A61K 47/64* (2017.08); *A61K 47/65* (2017.08); *A61K 47/66* (2017.08); *A61K 48/0008* (2013.01); *A61K 48/0041* (2013.01); *A61K 48/0083* (2013.01); *C07K 14/43586* (2013.01); *C12N 7/00* (2013.01); *C07K 2319/50* (2013.01); *C07K 2319/70* (2013.01); *C07K 2319/95* (2013.01); *C12N 2710/10043* (2013.01); *C12N 2710/10071* (2013.01); *C12N 2710/10332* (2013.01); *C12N 2710/10345* (2013.01); *C12N 2710/16033* (2013.01); *C12Y 207/01021* (2013.01)

(58) Field of Classification Search
  CPC .. A61K 47/48338; A61K 47/62; A61K 47/65; A61K 47/66; A61K 48/0008; A61K 48/0041; A61K 48/0083; C07K 14/00; C07K 14/43586; C07K 14/78
  See application file for complete search history.

(56) References Cited

U.S. PATENT DOCUMENTS

| | | | |
|---|---|---|---|
| 2011/0287517 A1* | 11/2011 | Steward | A61K 38/4893 435/220 |
| 2012/0149032 A1 | 6/2012 | Davis | |
| 2014/0086976 A1* | 3/2014 | Szalay | C12N 7/00 424/445 |
| 2014/0194370 A1* | 7/2014 | Cappello | A61K 38/39 514/21.2 |
| 2014/0206022 A1* | 7/2014 | Nuti | G01N 33/5005 435/7.92 |

OTHER PUBLICATIONS

Netzel-Arnett et al. Comparative Sequence Specificities of Human 72- and 92-kDa Gelatinases (Type IV Collagenases) and PUMP (Matrilysin). Biochemistry. 1993, vol. 32, No. 25, pp. 6427-6432.*
Gustafson et al. Synthesis and Characterization of a Matrix-Metalloproteinase Responsive Silk-Elastinlike Protein Polymer. BioMacromolecules. Jan. 31, 2013, vol. 14, pp. 618-625.*
137965353.6, Extended European Search Report, dated Nov. 13, 2015, 7 pages.
Greish, et al., "Silk-elastinlike protein polymers improve the efficacy of adenovirus thymidine kinase enzyme prodrug therapy of head and neck tumors", J Gene Med. 12(7), Jul. 2010, pp. 572-579.
Gustafson, et al., "Silk-Elastinlike Hydrogel Improves the Safety of Adenovirus-Mediated Gene-Directed Enzyme-Prodrug Therapy", Mol. Pharm. 7(4), Aug. 2, 2010, pp. 1050-1056.
PCT/US2013/043487, International Preliminary Report and Patentability, dated Dec. 2, 2014, 7 pages.
Vartak, et al., "Matrix metalloproteases; Underutilized targets for drug delivery", Journal of Drug Targeting 15(1), Jan. 2007, pp. 1-20.
Vemula, et al., "Self-assembled prodrugs: an enzymatically triggered drug-delivery platform", Biomaterials 30, 2009, pp. 383-393.
Chang et al., "Nanochemical stimulus accelerates and directs the self assembly of silk-elastin-like nanofibers" J. Am. Chem. Soc. Feb. 16, 2011; 133(6); 1745?1747; abstract, p. 2 para 2.
Dinerman et al., "Swelling behavior of a genetically engineered silk-elastinlike protein polymer hydrogel" Biomaterials 23 (2002) 4203?4210; abstract.
International Search Report Issued in PCT/US2013/043487 dated Jan. 7, 2014.
Written Opinion Issued in PCT/US2013/043487 dated Jan. 7, 2014.

* cited by examiner

FIG 1 : Rationale for SELP-Mediated GDEPT system

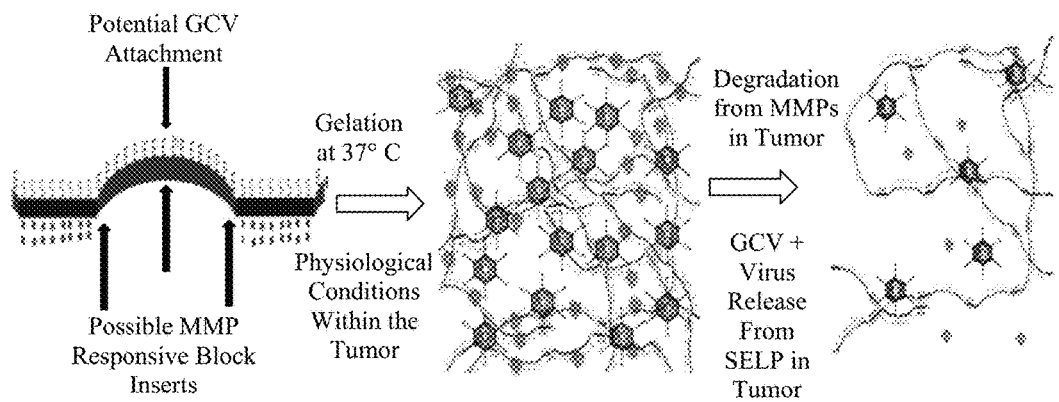

FIG 2 : Single Amino Acid Abbreviation Representations of Three SELP Structures

| | Single amino acid abbreviation representations of three SELP structures<br>Silk Unit: GAGAGS    Elastin Unit: GVGVP<br>Lysine-Substitited Elastin Unit: GKGVP |
|---|---|
| SEQ ID NO : 19 | SELP47K: MDPVVLQRRDWENPGVTQLVRLAAHPPFASDPMGAGS GAGS[(GVGVP)$_4$GKGVP(GVGVP)$_3$(GAGAGS)$_4$]$_{12}$(GVGVP)$_4$GKGVP (GVGVP)$_2$(GAGAGS)$_2$GAGAMDPGRYQDLRSHHHHHH |
| SEQ ID NO : 20 | SELP415K: MDPVVLQRRDWENPGVTQLVRLAAHPPFASDPMGA GSGAGS[(GVGVP)$_4$GKGVP(GVGVP)$_{11}$(GAGAGS)$_4$]$_7$(GVGVP)$_{11}$ GKGVP(GVGVP)$_4$(GAGAGS)$_2$GAGAMDPGRYQDLRSHHHHHH |
| SEQ ID NO : 21 | SELP815K: MDPVVLQRRDWENPGVTQLNRLAAHPPFASDPM[GAGS (GAGAGS)$_2$(GVGVP)$_4$GKGVP(GVGVP)$_{11}$(GAGAGS)$_5$GAGA]$_6$MDPGRY QDLRSHHHHHH |

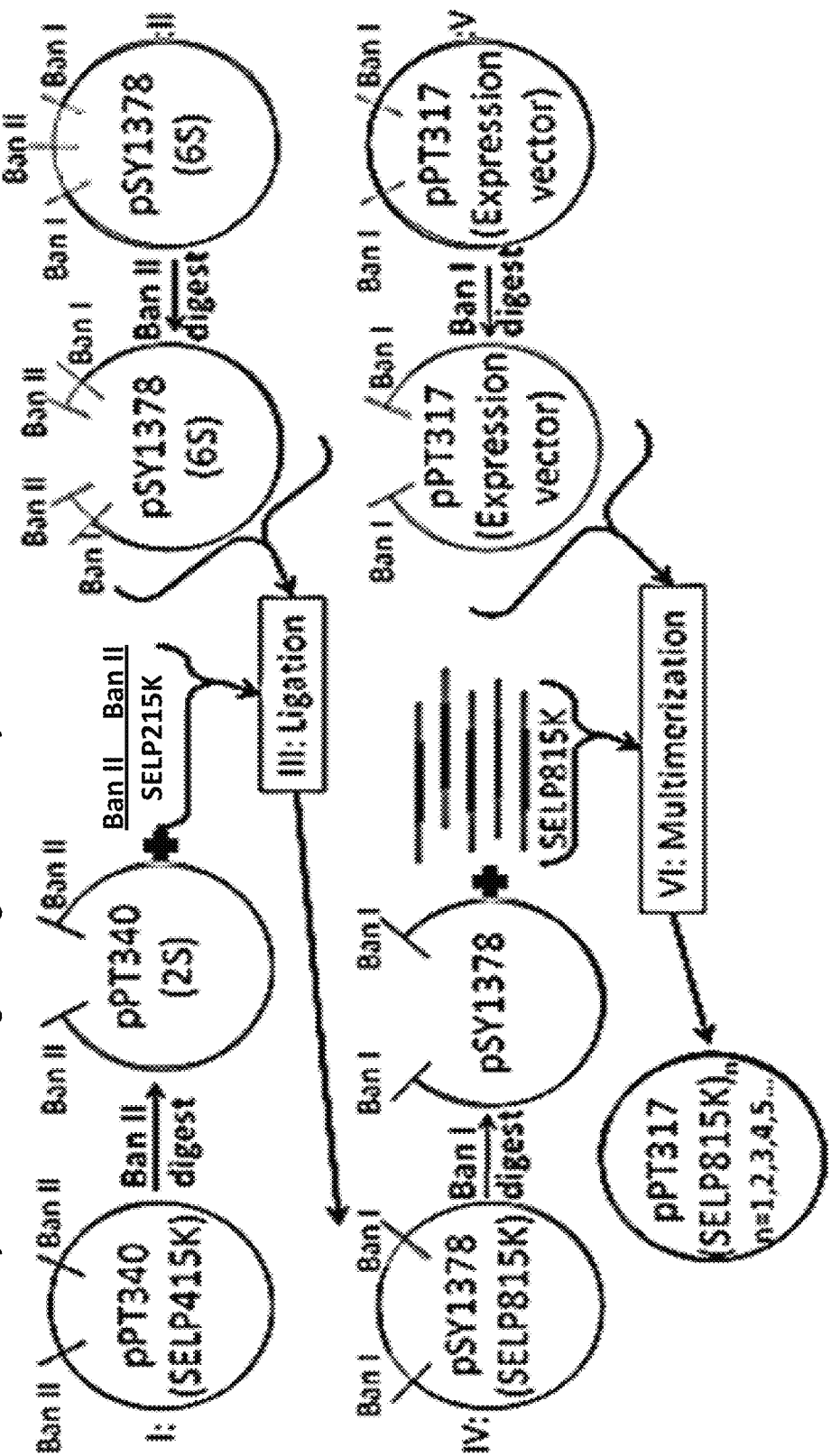
FIG 3: Summary of Molecular Engineering of SELP Polymers

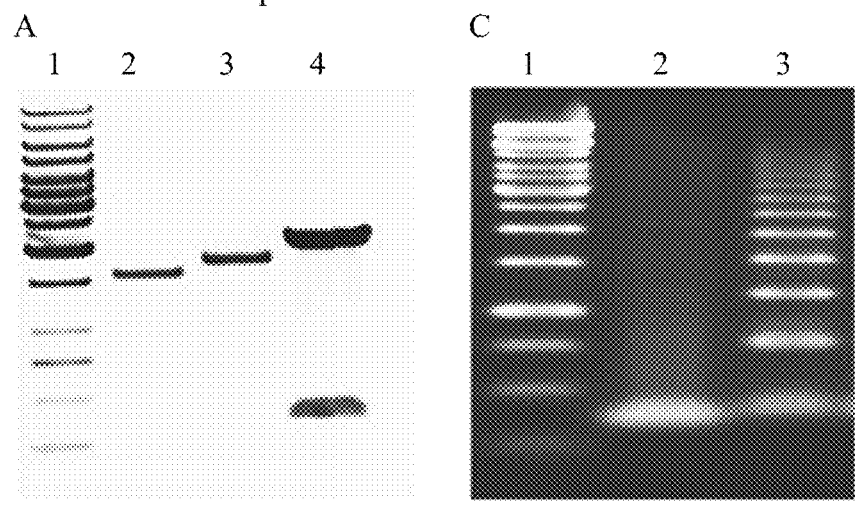

FIG 4: Gel Electrophoresis of SELP-815K Monomer

A 1  2  3  4

C 1  2  3

B
SEQ ID NO: 22    GGCACCCGCTCCGCTTCCTGCTCCAGCACCTGAGCCAGCGCCTGC
GCCGGATCCTGCGCCCGCGCCAGAGCCCGCGCCTGCGCCGCTACC
AGCACCCGCTCCCGGGACGCCAACTCCAGGAACTCCTACACCCGG
CACTCCTACTCCCGGTACGCCTACTCCTGGTACGCCAACTCCAGG
AACTCCTACACCCGGCACTCCTACTCCCGGTACGCCTACTCCTGGT
ACGCCTACACCTGGTACTCCAACGCCCGGCACACCTACCCCCGGA
ACACCTTTTCCAGGTACACCAACTCCCGGAACGCCTACACCCGGA
ACACCGACACCGTGCACTCCAACACCAGAGCCCGCGCCAGCTCCA
GAACCGGCTCCTGCACCGCTGCCGGCACC

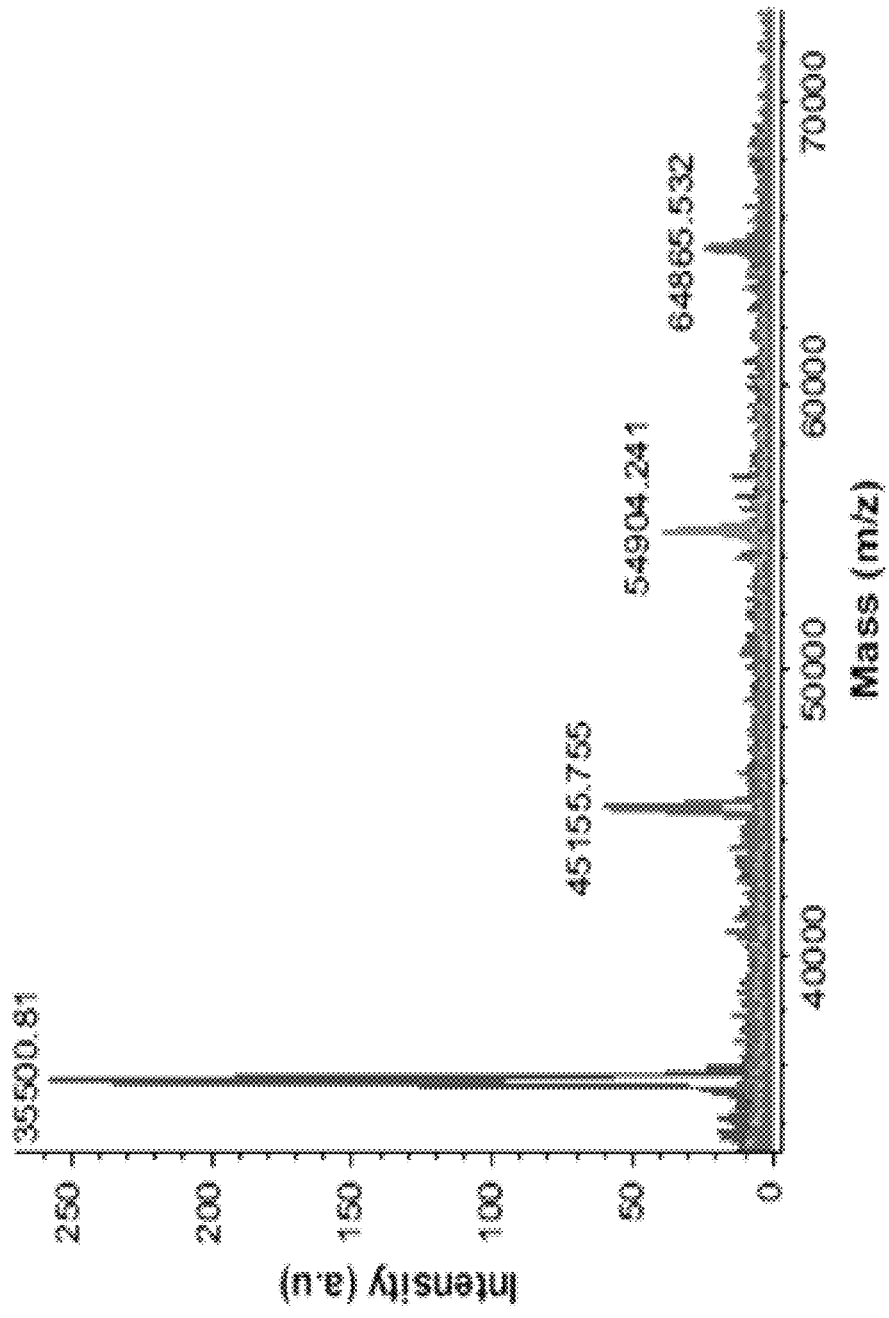
FIG 5: MALDI-TOF Mass Spectrometry Results for SELP815K Synthesis

FIG 6: AFM Image of Linear SELP415K on Mica Surface
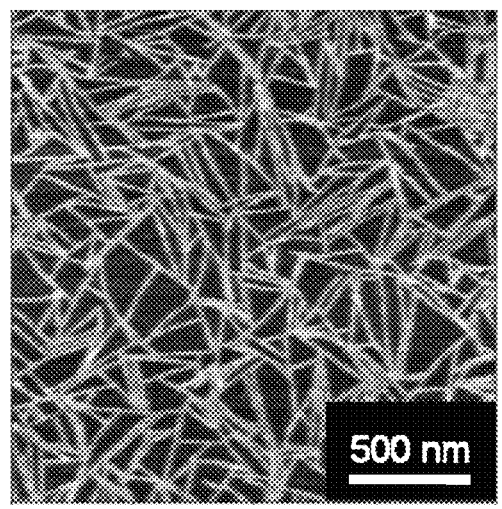

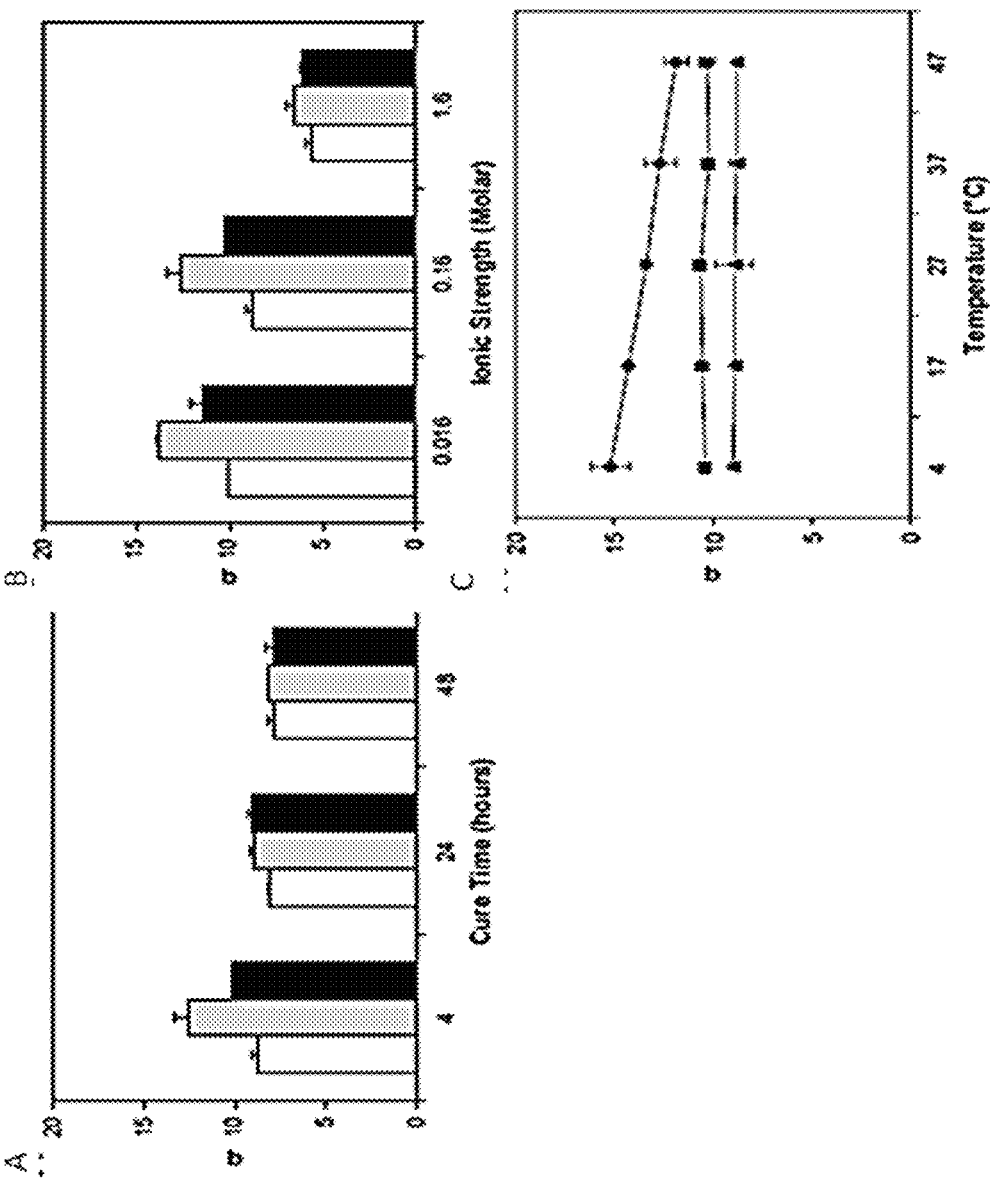
FIG 7: Structure And Environmental Dependence In Swelling Behavior Of SELP Hydrogels FIG 8: DMA of SELP Hydrogels
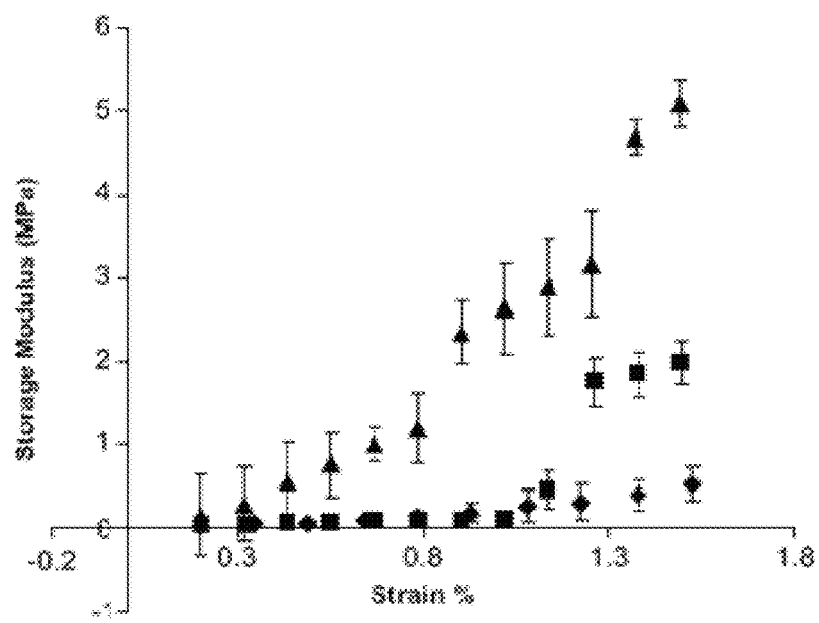
FIG 9: SANS Plot of 12wt% Used To Infer Hydrogel Structural Changes
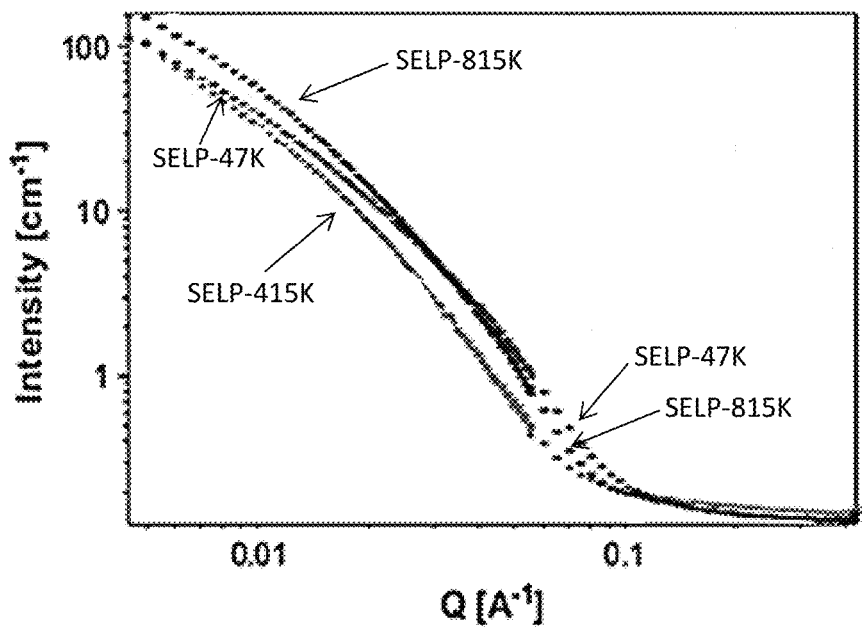

FIG 10: Typical Time, Structure and Concentration, Dependent Release of Adenoviruses from SELP Hydrogels
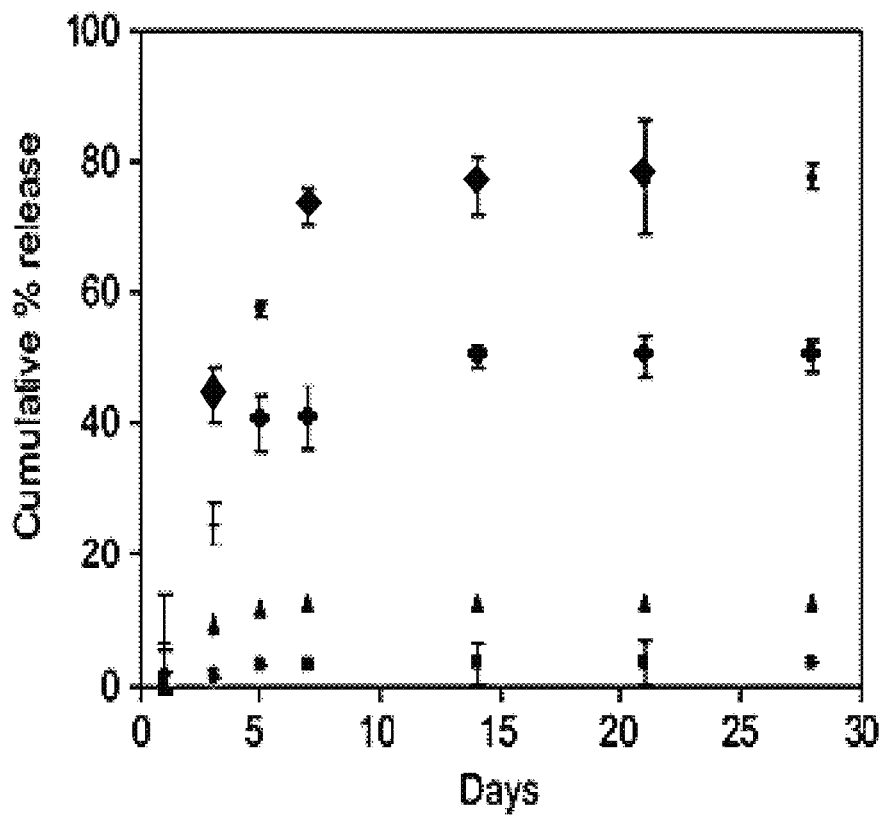
FIG 11: Structure Dependent Degradability of SELP Hydrogels by Elastase
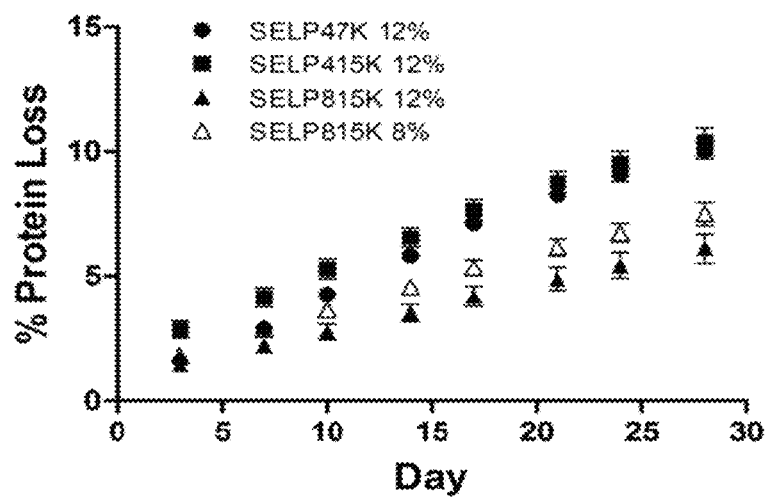

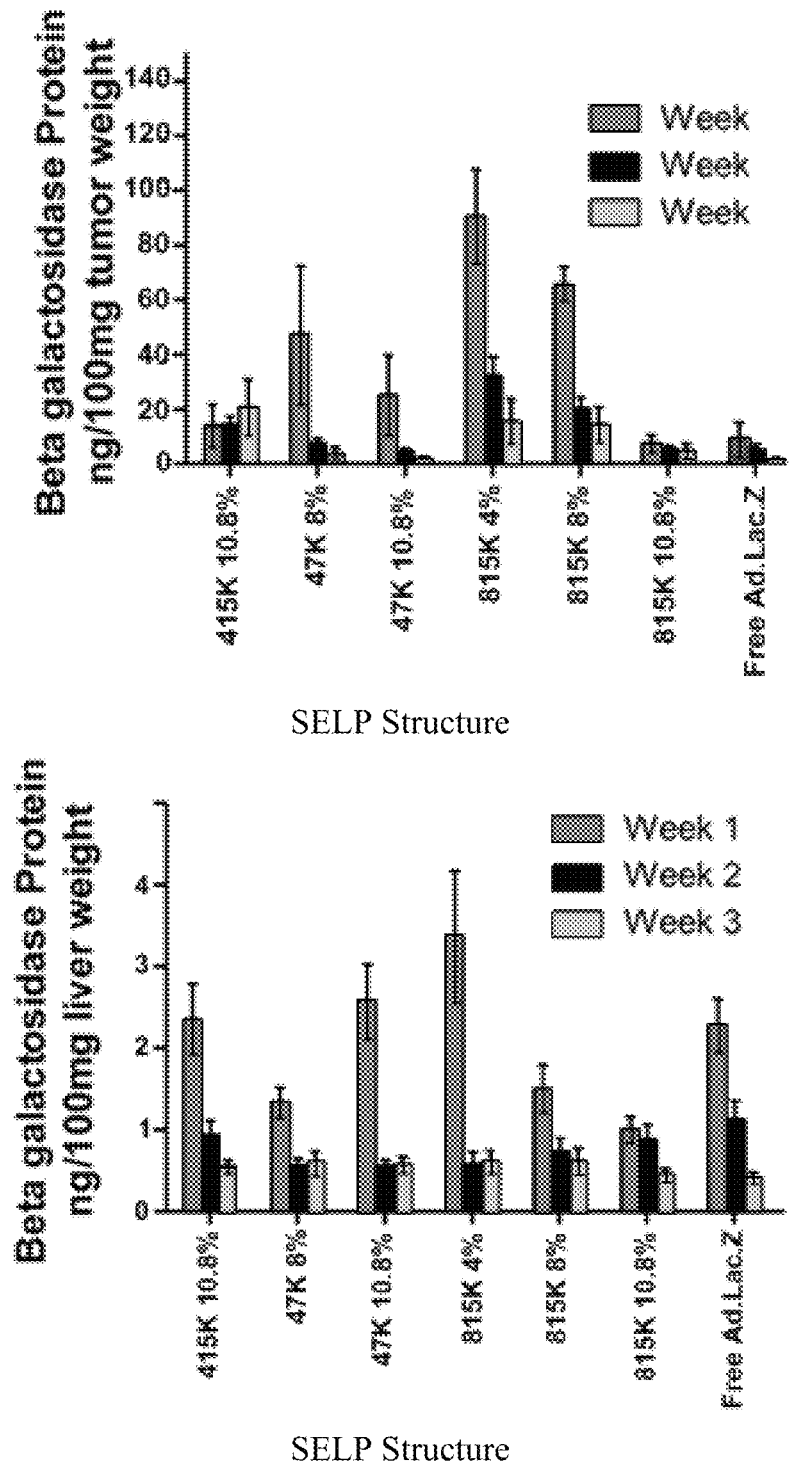
FIG 12: β-Gal Levels For Each Examined Polymer In The Tumors

FIG 12: β-Gal Levels For Each Examined Polymer In The Tumors (Cont.)
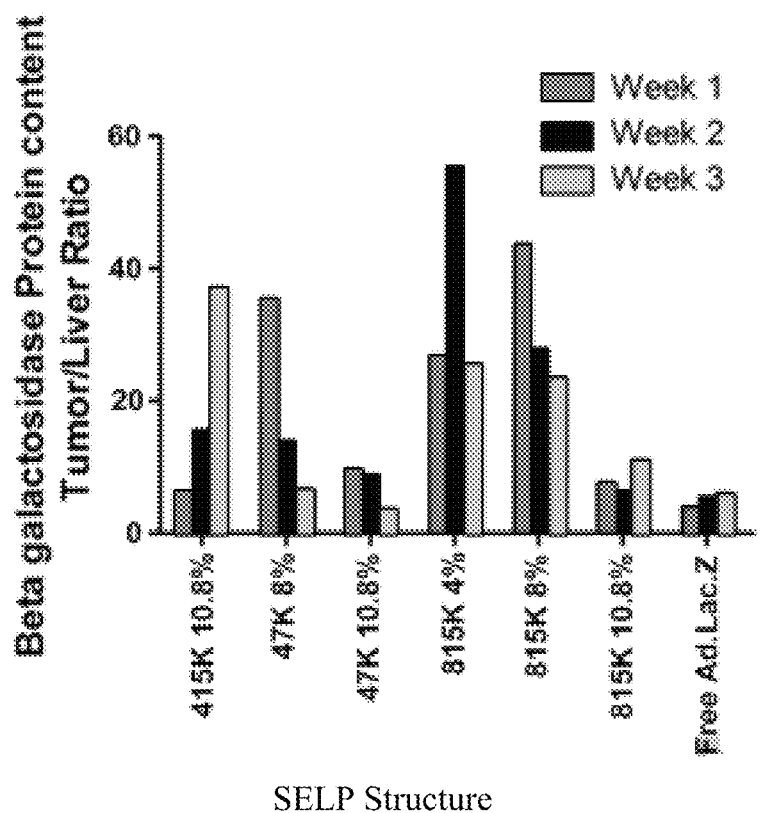
FIG 13: Map of Recombinant Ad HSVtk Luc.

FIG 14A: Time Dependent Reduction In Tumor Volume
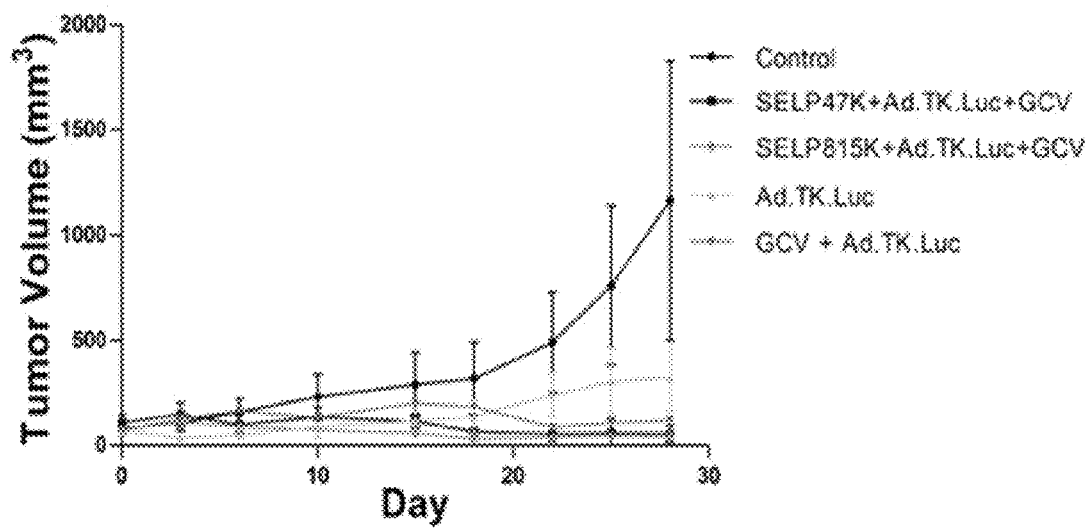
FIG 14B: Time Dependent Reduction In Tumor Volume
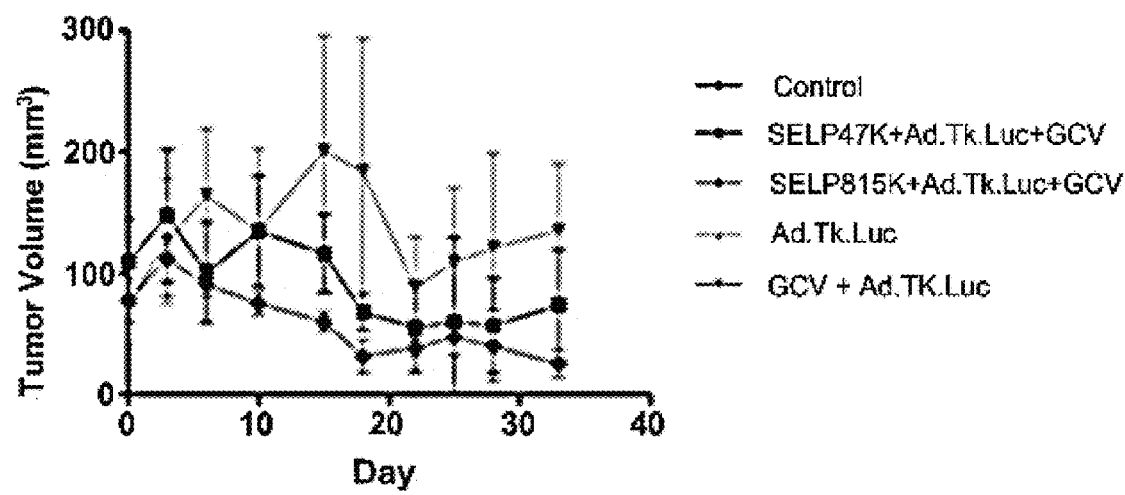

FIG 15: Animal Weight Over Time In Nude Mice Bearing JHU-022 Head and Neck Cancer Cells
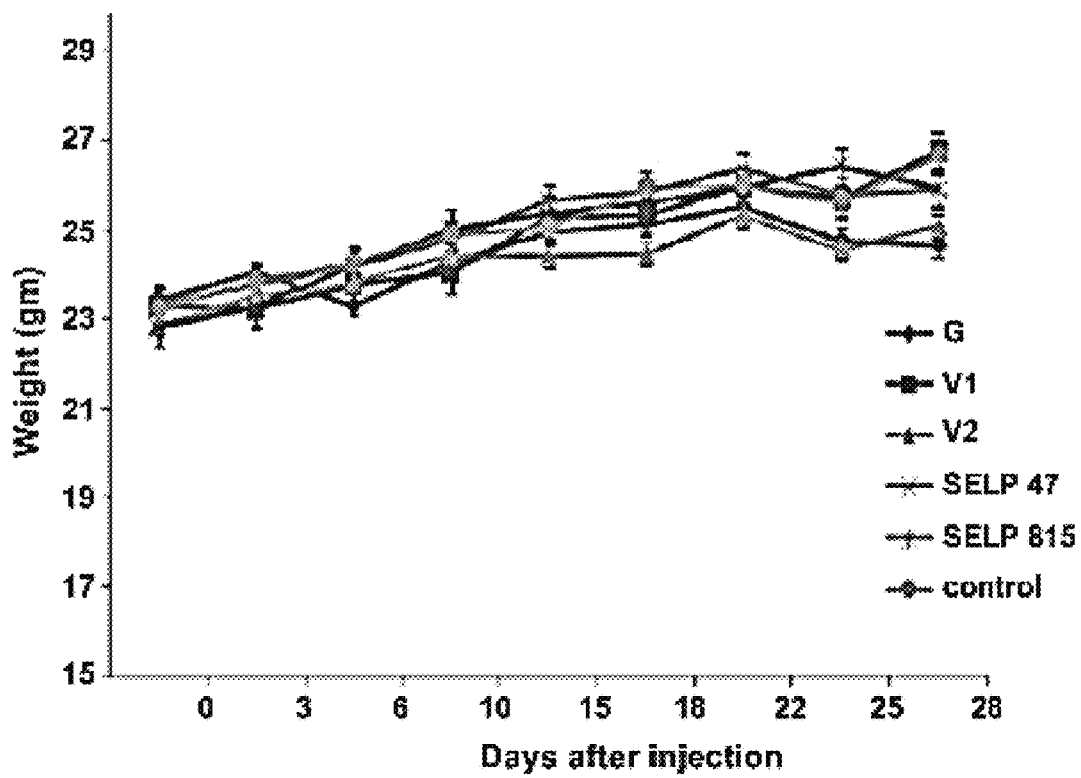
FIG 16: Tumor Size Progression *in vivo*
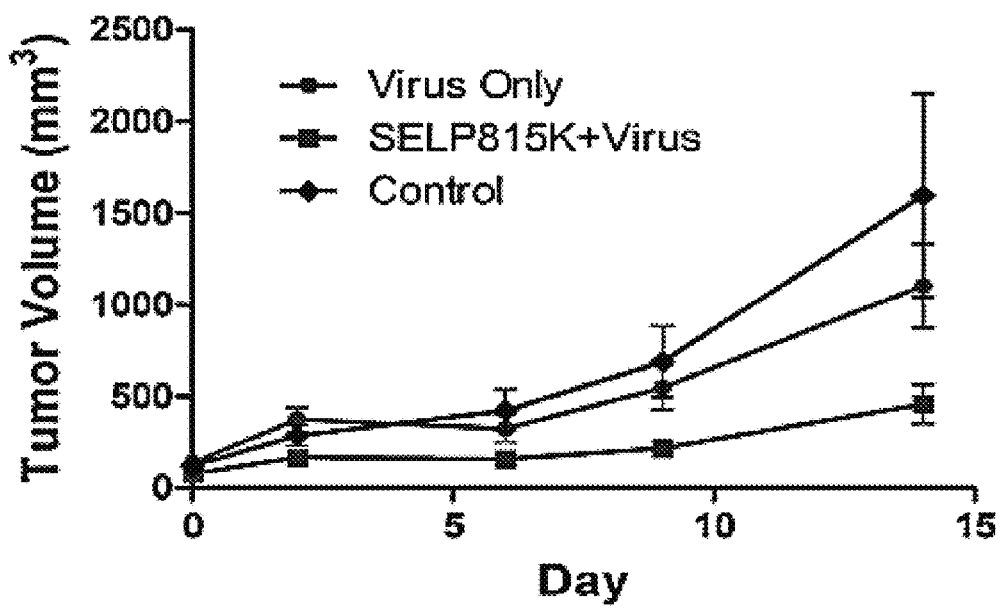

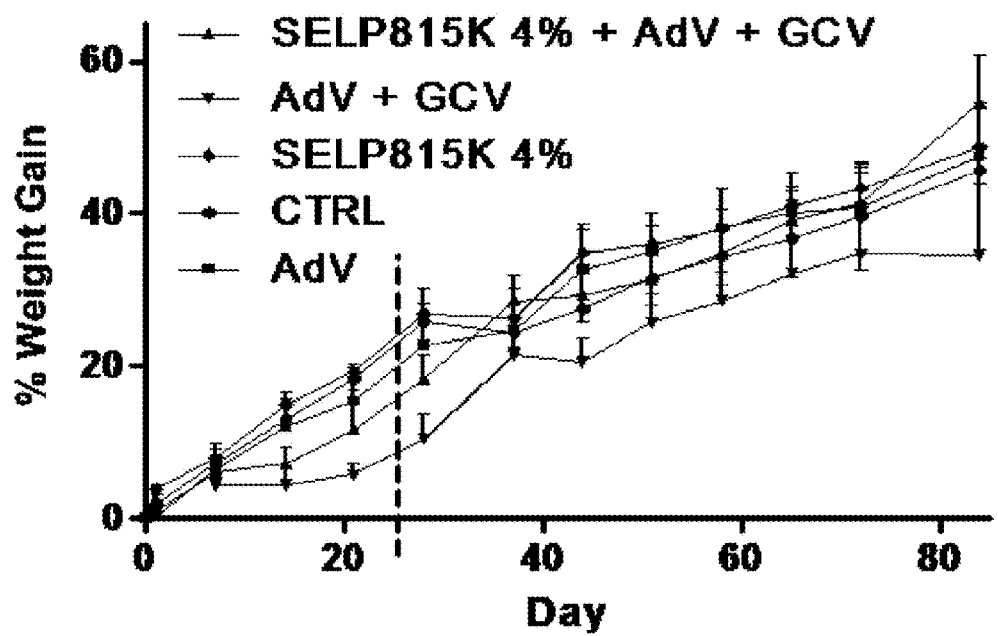
FIG 17: Subchronic Toxicity Study in Immunocompetent Mice : Week 4 of 12

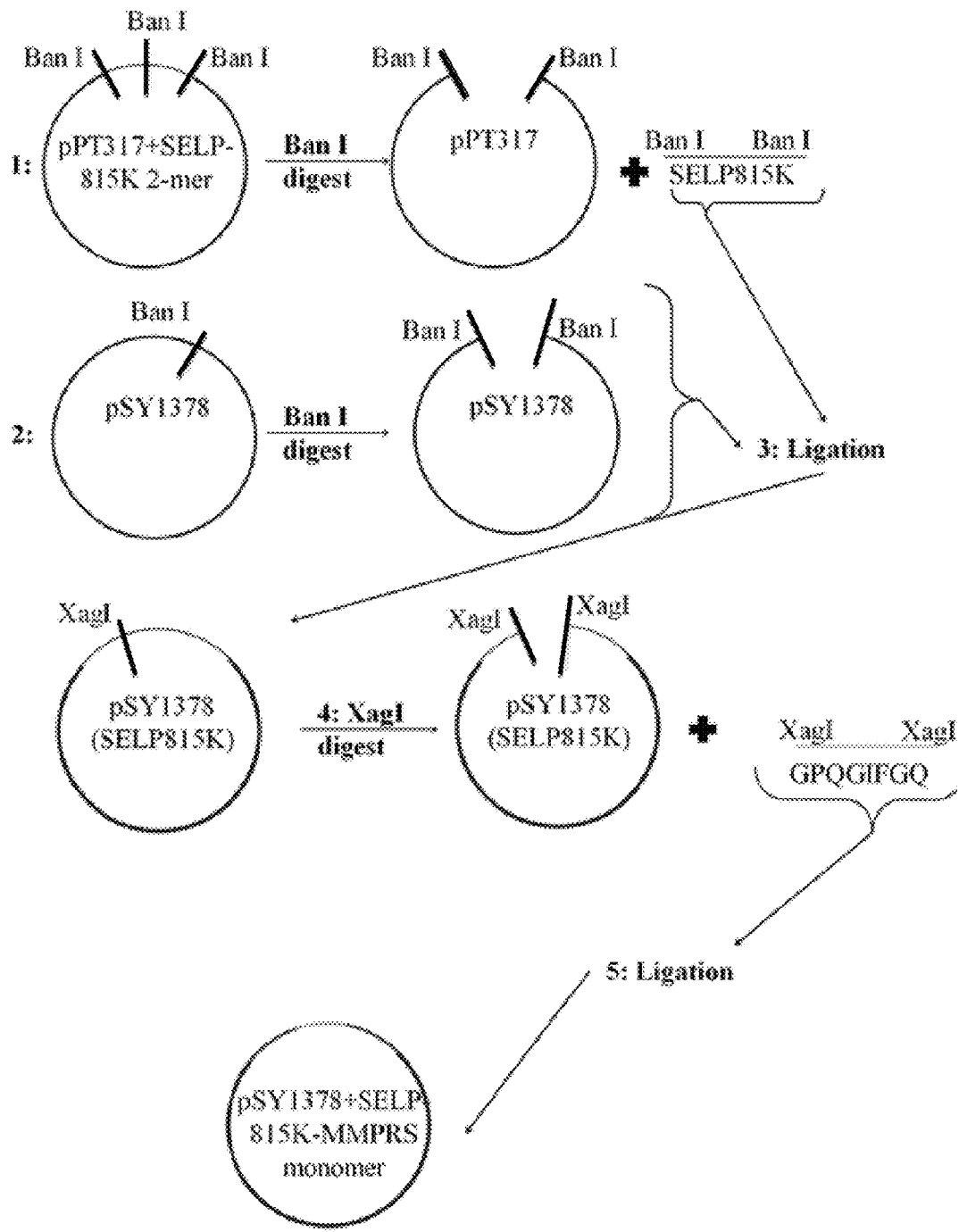
FIG 18: Synthesis of SELP815K-MMPRS Monomer Gene Segment

FIG 19: SDS-PAGE Analysis of 10 nM MMP-2 Digest of SELP815K Over Time.
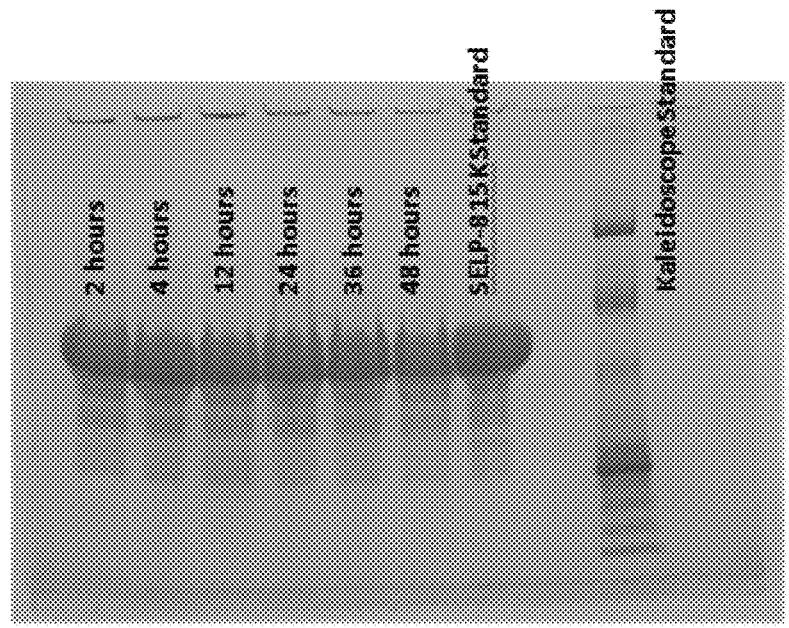
FIG 20: SDS-PAGE Analysis of 10 nM MMP-2 digest of SELP815K-MMPRS Over Time.
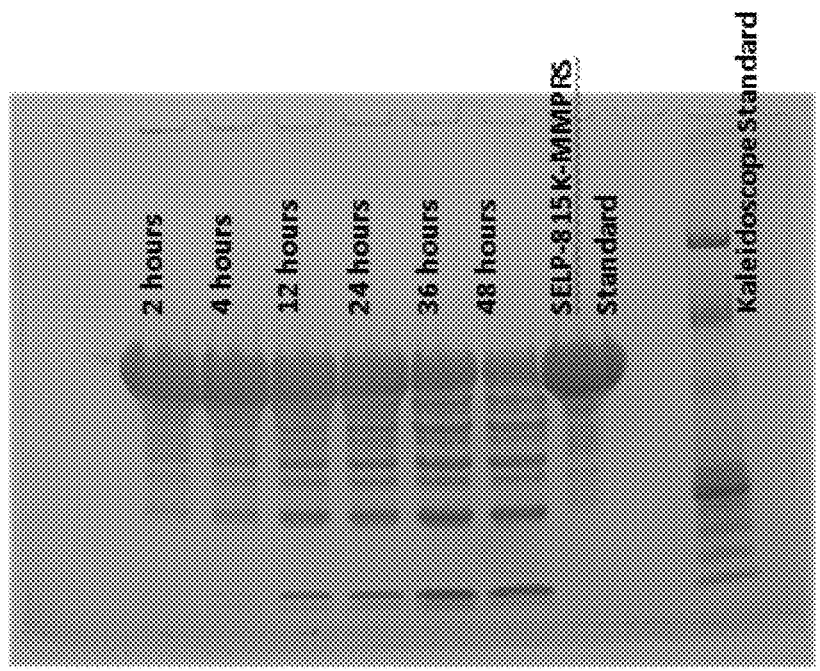

FIG 21: SDS-PAGE Analysis of 40 nM MMP-2 digest of SELP815K Over Time
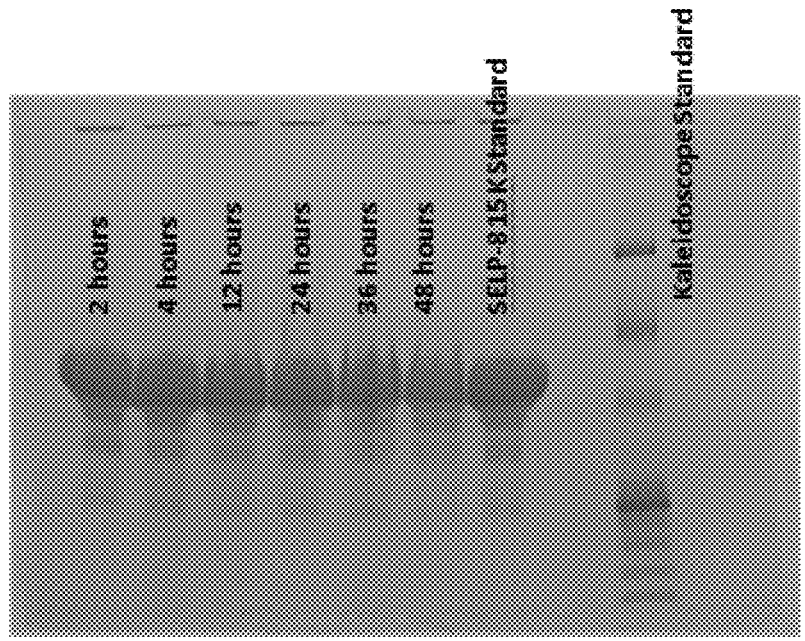
FIG 22: SDS-PAGE analysis of 40 nM MMP-2 digest of SELP815K-MMPRS Over Time
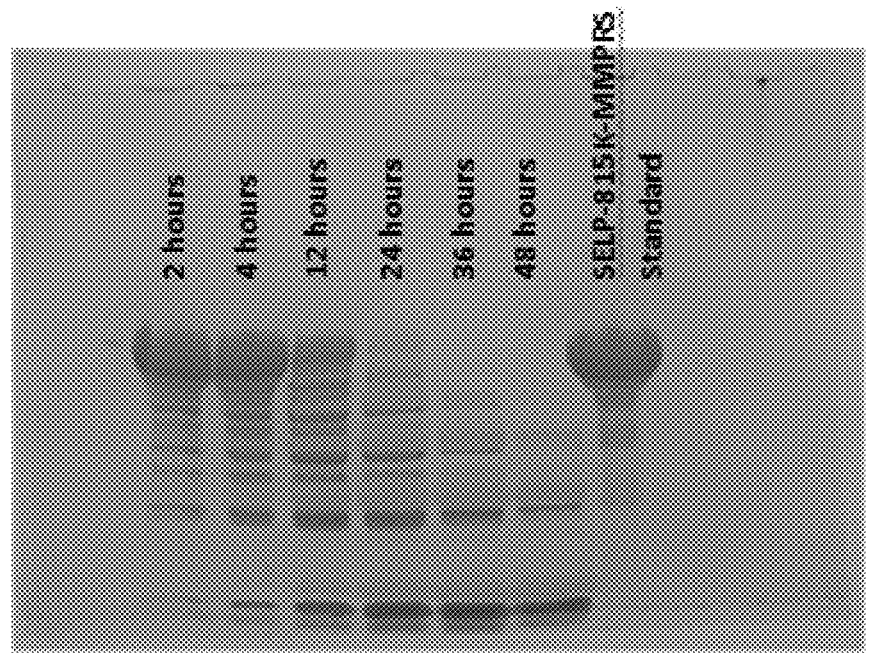

FIG 23 : SDS-PAGE Analysis of 10 nM MMP-9 digest of SELP815K Over Time
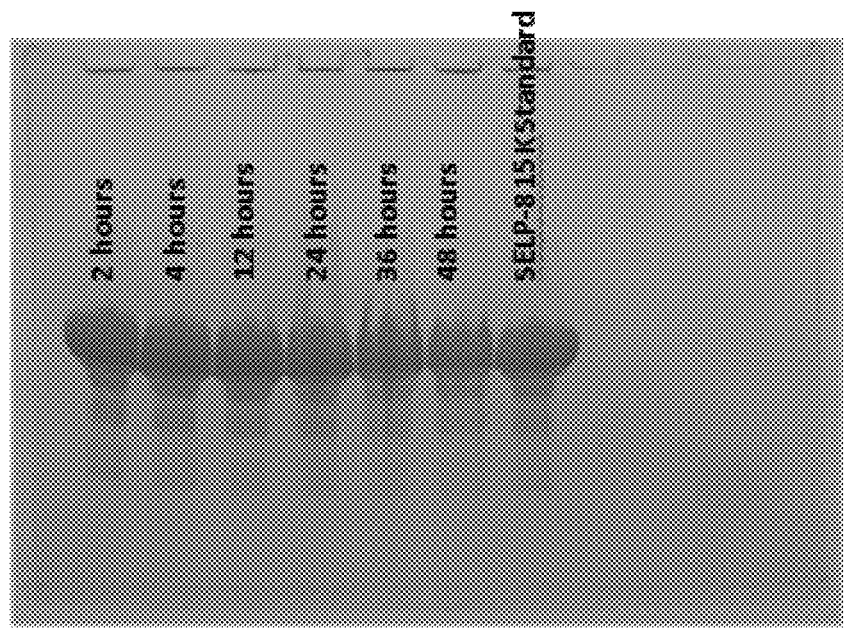
FIG 24 : SDS-PAGE Analysis of 10 nM MMP-9 digest of SELP815K-MMPRS Over Time
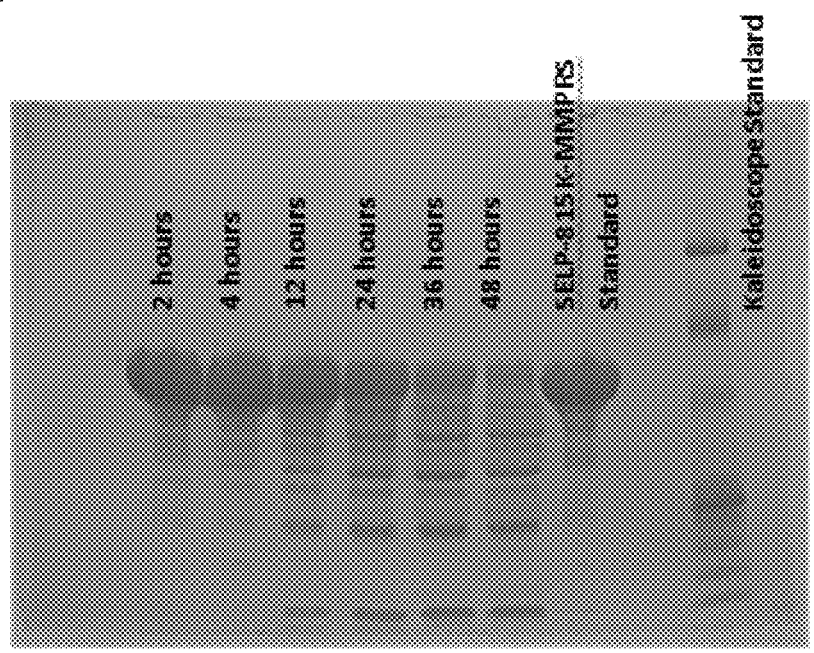

FIG 25 : SDS-PAGE Analysis of 40 nM MMP-9 digest of SELP815K Over Time
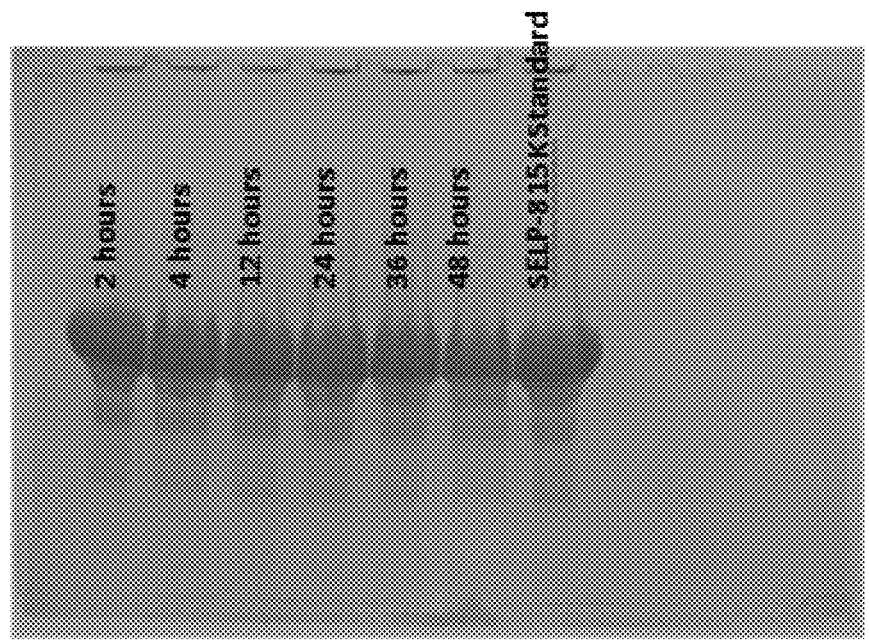
FIG 26 : SDS-PAGE Analysis of 40 nM MMP-9 digest of SELP815K-MMPRS Over Time
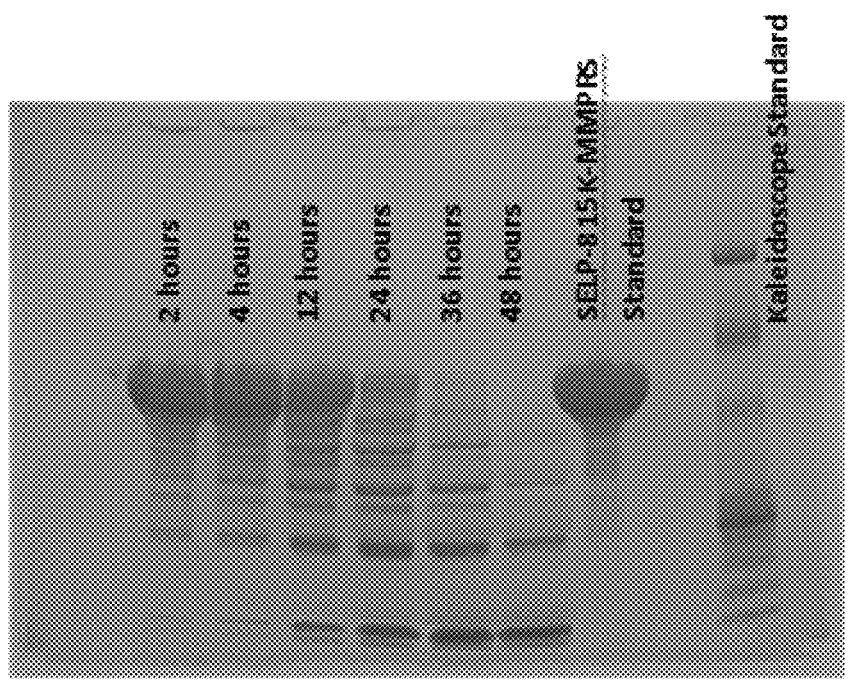

FIG 27: Total Degradation at 2 weeks for SELP815K±MMPRS Hydrogels
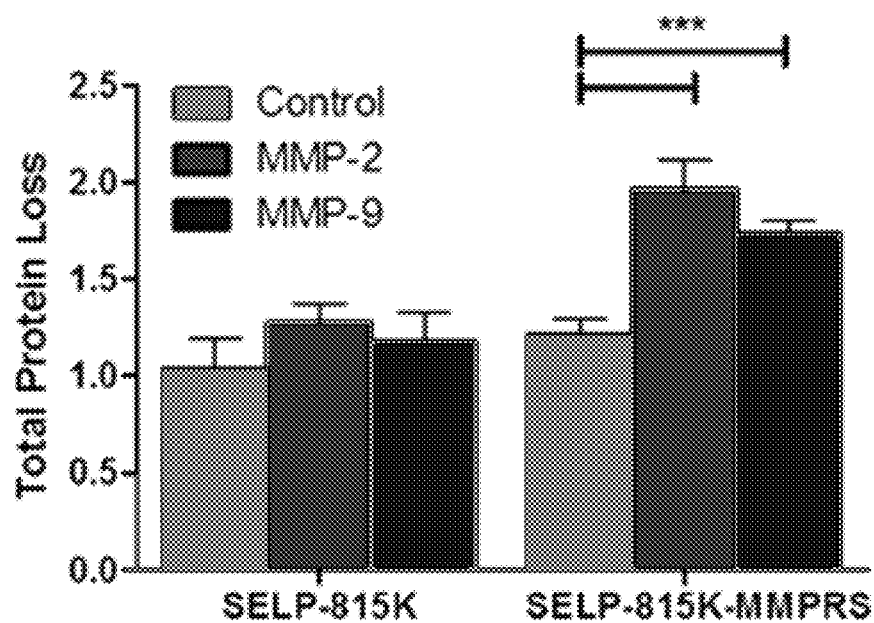
FIG 28: Protein loss over time for SELP815K hydrogels
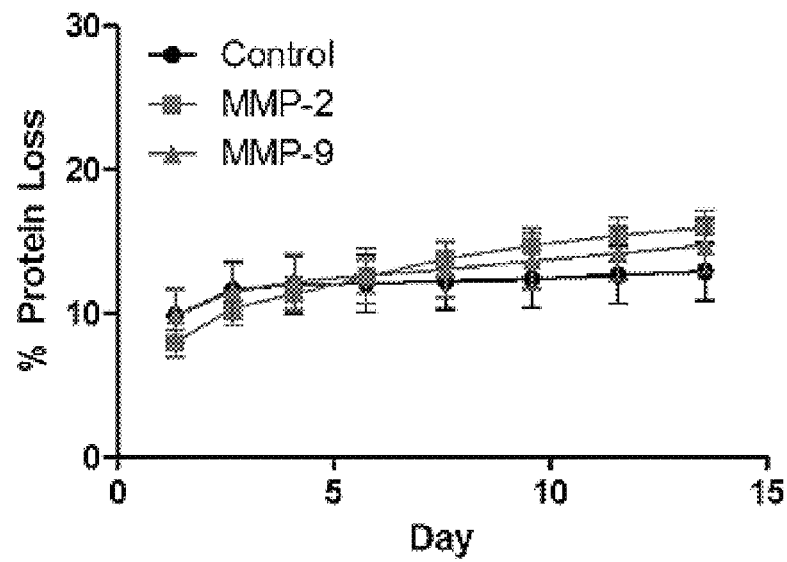

FIG 29: Protein Loss Over Time for SELP815K-MMPRS Hydrogels
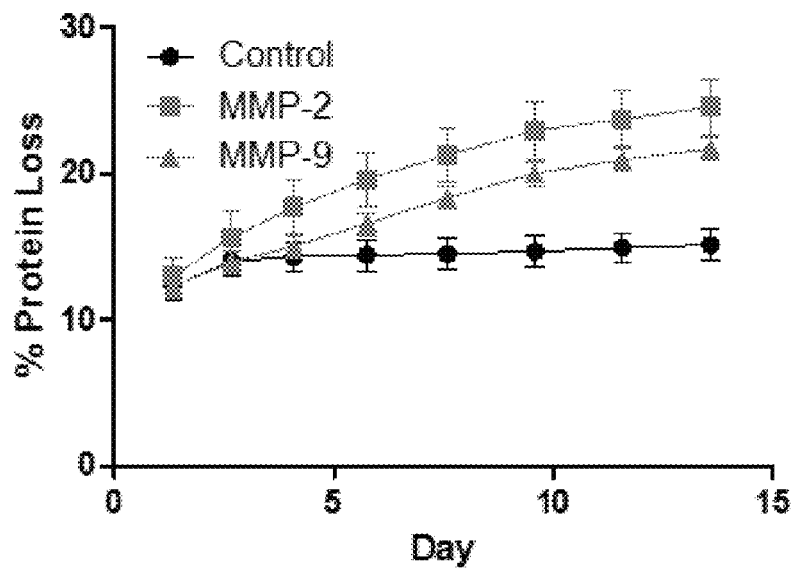
FIG 30: Compressive Modulus of Hydrogels in the Presence and Asence of MMPs
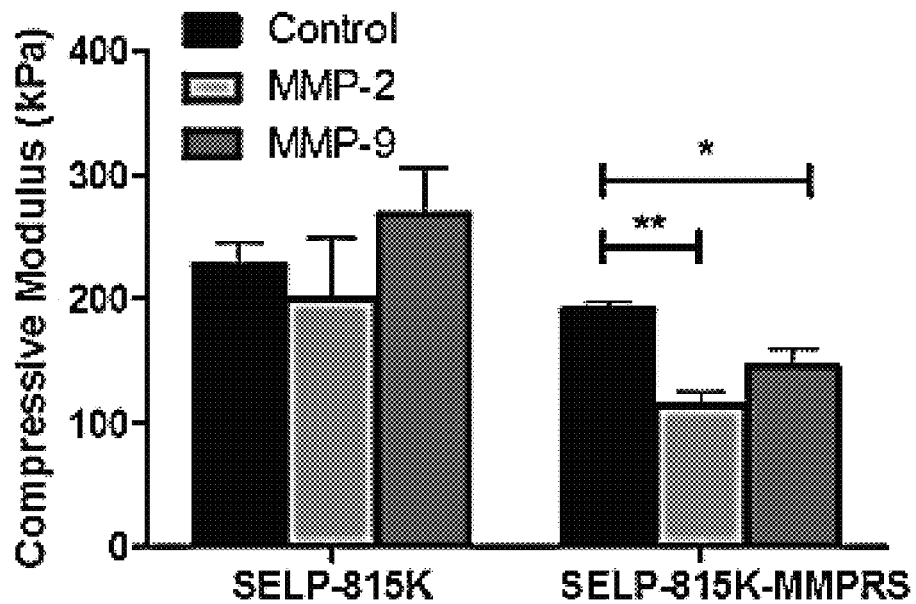

FIG 31: Total Release of 100nm Nanoparticles from SELP815K±MMPRS Hydrogels
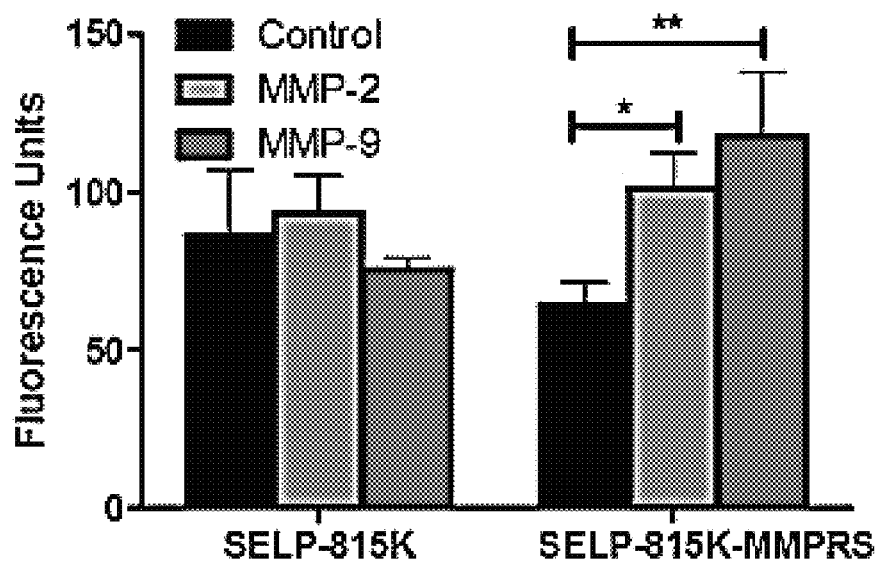
FIG 32: Nanoparticle Release Over Time for SELP815K Hydrogels
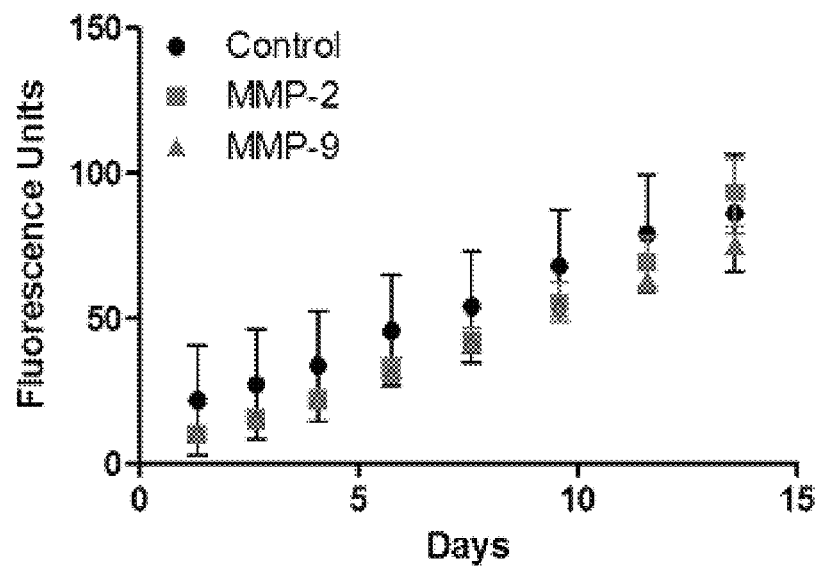

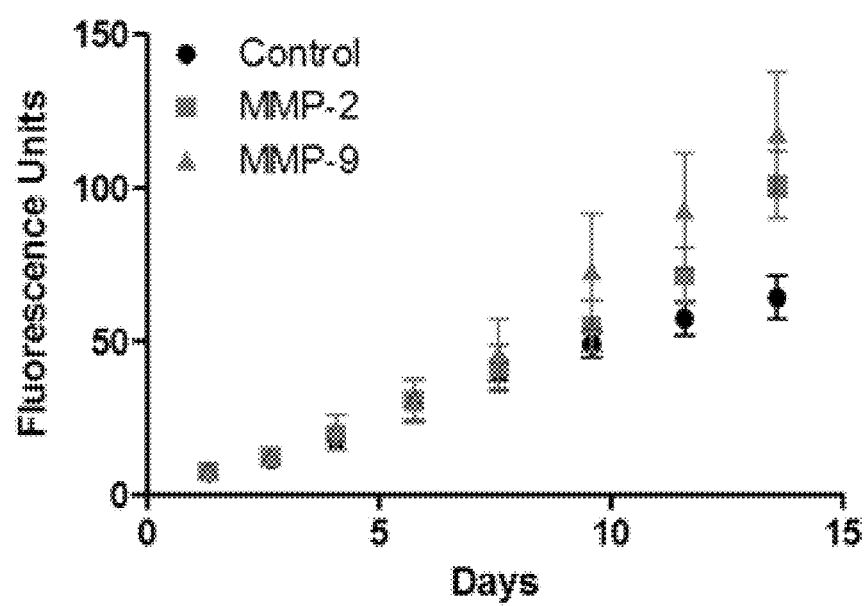
FIG 33 : Nanoparticle Release Over Time for SELP815K-MMPRS Hydrogels

MATRIX METALLOPROTEINASE CLEAVABLE PROTEIN POLYMERS FOR CANCER GENE THERAPY

RELATED APPLICATIONS

This application is a national stage entry of PCT/US2013/043487, filed May 30, 2013, which claims priority to U.S. Provisional Application No. 61/689,285, filed May 30, 2012, each of which is incorporated herein by reference in its entirety.

STATEMENT REGARDING FEDERALLY SPONSORED RESEARCH

This invention was made with government support under Grant Number R01 CA107621 awarded by the National Institutes of Health. The government has certain rights in the invention.

TECHNICAL FIELD

The present disclosure relates generally to the field of drug delivery methods comprising polymers. The system may be used to prevent or treat cancer, inflammatory diseases, wounds, and other pathological conditions associated with elevated levels of proteases including matrix metalloproteinases (MMPs).

BRIEF DESCRIPTION OF THE DRAWINGS

FIG. 1 illustrates the rationale behind one embodiment of the disclosed method of SELP-mediated gene delivery enzyme prodrug therapy (GDEPT) using MMP-responsive hydrogels.

FIG. 2 provides the amino acid structure of three SELPs: SEQ ID NO. 19, SEQ ID NO. 20, and SEQ ID NO. 21.

FIG. 3 provides a summary of the molecular engineering of the SELP polymers of FIG. 2.

FIG. 4A shows the progression of SELP-815K monomer gene segment synthesis via gel electrophoresis.

FIG. 4B illustrates the DNA sequence for the monomer gene segment in between the two BanI restriction sites. This sequence is provided in the Sequence Listing as SEQ ID NO. 22.

FIG. 4C shows the formation of the polymer gene segment.

FIG. 5 illustrates MALDI-TOF mass spec results for the SELP815K synthesis before colony selection.

FIG. 6 illustrates AFM images of linear SELP415K on a mica surface.

FIG. 7A provides a graphical illustration of the effects of cure time and polymer structure on swelling ratio.

FIG. 7B provides a graphical illustration of the swelling ratio dependence of SELP hydrogels on ionic strength of release medium.

FIG. 7C provides a graphical illustration of the swelling ratio dependence of SELP hydrogels on temperature.

FIG. 8 provides a graphical illustration of the DMA of the SELP hydrogels.

FIG. 9 provides a SANS plot of 12 wt % SELPs used to infer hydrogel structural changes.

FIG. 10 provides a graphical illustration of a typical time, structure and concentration dependent release of adenoviruses from SELP hydrogels.

FIG. 11 provides a graphical illustration of the time dependence of elastase degradation leading to soluble fraction release for hydrogels composed of three different SELP structures.

FIG. 12 provides a graphical illustration of β-gal levels for each examined polymer in the tumors, livers, and the liver/tumor ratios.

FIG. 13 shows a map of recombinant Ad.HSVtk.Luc.

FIG. 14A provides a graphical illustration of changes in tumor size in nude mice over time.

FIG. 14B provides a graphical illustration of changes in tumor size in nude mice over time with regard to two of the groups shown in FIG. 14A.

FIG. 15 provides a graphical illustration of animal weight over time in nude mice bearing JHU-022 head and neck cancer cells.

FIG. 16 provides a graphical illustration of tumor size progression in immunocompetent mice in vivo.

FIG. 17 provides a graphical illustration of the results of the first month of the 12 week subchronic toxicity study in immunocompetent mice.

FIG. 18 illustrates the synthesis of the SELP815K-MM-PRS monomer gene segment. SEQ ID NO. 21 (SELP815K) is first ligated into a plasmid, then the sequence GPQGIFGQ (SEQ ID NO. 10) is ligated into the plasmid containing SELP815K.

FIG. 19 illustrates SDS-PAGE analysis of 10 nM MMP-2 digest of SELP815K over time.

FIG. 20 illustrates SDS-PAGE analysis of 10 nM MMP-2 digest of SELP815K-MMPRS over time.

FIG. 21 illustrates SDS-PAGE analysis of 40 nM MMP-2 digest of SELP815K over time.

FIG. 22 illustrates SDS-PAGE analysis of 40 nM MMP-2 digest of SELP815K-MMPRS over time.

FIG. 23 illustrates SDS-PAGE analysis of 10 nM MMP-9 digest of SELP815K over time.

FIG. 24 illustrates SDS-PAGE analysis of 10 nM MMP-9 digest of SELP815K-MMPRS over time.

FIG. 25 illustrates SDS-PAGE analysis of 40 nM MMP-9 digest of SELP815K over time.

FIG. 26 illustrates SDS-PAGE analysis of 40 nM MMP-9 digest of SELP815K-MMPRS over time.

FIG. 27 provides a graphical illustration of total degradation at 2 weeks for SELP815K±MMPRS hydrogels.

FIG. 28 provides a graphical illustration of protein loss over time for SELP815K hydrogels.

FIG. 29 provides a graphical illustration of protein loss over time for SELP815K-MMPRS hydrogels.

FIG. 30 provides a graphical illustration of compressive modulus of hydrogels in the presence and absence of MMPs.

FIG. 31 provides a graphical illustration of total release of 100 nm nanoparticles from SELP815K±MMPRS hydrogels in the presence and absence of MMPs.

FIG. 32 provides a graphical illustration of nanoparticle release over time for SELP815K hydrogels.

FIG. 33 provides a graphical illustration of nanoparticle release over time for SELP815K-MMPRS hydrogels.

BRIEF DESCRIPTION

The present disclosure relates generally to the field of drug delivery methods for treating cancer, inflammatory diseases, wounds, and other tissues that express elevated levels of proteases, including matrix metalloproteinases (MMPs). More specifically, the present disclosure relates to the use of recombinantly synthesized protein polymers, including silk-elastin-like copolymers, with protease cleavage sites engineered into the protein copolymer. This material may be used to deliver polynucleotides, such as an adenovirus, or carriers thereof, and other large and small molecular therapeutics, into a target tissue in a controlled, safe, and effective manner. The polynucleotide may encode a therapeutic peptide, protein, or enzyme that activates a prodrug that is administered with the material. these sequences in a precise location along the polymer backbone using recombinant techniques. These MMP responsive sequences may be placed in specific locations along the polymer backbone using recombinant techniques.

DETAILED DESCRIPTION

The problem of safe and efficient delivery of nucleic acids and other bioactive agents to target cells in vivo is a significant clinical obstacle. Properly controlled delivery of bioactive agents has the potential to alleviate adverse effects and allow for the best possible treatment conditions in terms of patient compliance, reduced toxicity, and increased efficacy. This disclosure provides a solution to the problem of controlling the introduction of bioactive agents into a tissue in a localized manner which improves efficacy as well as safety of the therapy.

One method by which transfer of bioactive agents can be controlled is using matrix-mediated gene delivery (MMGD). MMGD is the use of a biomaterial to control the delivery of a bioactive product in a spatiotemporal fashion. MMGD generally involves encapsulation of the vectors into polymeric matrices that protect the patient and vector while releasing the appropriate dose for the required amount of time. The advantages of polymeric delivery include: (a) the ability to manipulate release profile, delivering the cargo to tissue in a sustained and predictable manner, (b) the ability to localize delivery to a specific tissue such as, but not limited to, a tumor, and (c) potential for delivery of more than one agent for combination therapy. Such techniques may be also used to deliver bioactive agents other than nucleic acids. The majority of polymers that have been used in controlled drug and gene delivery to-date are either synthesized by traditional chemical synthetic techniques, processed from natural sources or a combination of the above.

Chemical synthetic techniques used for delivery of bioactive agents generally produce random copolymers with unspecified monomer sequences and statistical distribution of molecular weight and monomer composition. This is a distinct disadvantage because polymers with various lengths and sequences have different physicochemical properties and loading efficiencies, leading to variations in release. Moreover, chemically synthesized polymers generally contain solvents and monomer residues which may not be biocompatible with either the host or the delivered bioactive agents. Natural polymers such as collagen matrices used in delivery of bioactive agents may suffer from the difficulty of introducing new functional motifs (e.g., stimuli-sensitive, biodegradable, and biorecognizable) to allow suitable control over release and mechanical properties. Techniques for making polymers with well-defined characteristics are needed to enable the controlled delivery of viruses, peptides, small molecular weight drugs, and other bioactive agents in a predictable manner and in response to specific local stimuli.

This disclosure illustrates the design of new polymers for delivery of bioactive agents in response to local production of proteases, including, in some specific examples, matrix metalloproteinases (MMPs). The subject matter of this disclosure may be used to enhance the efficacy of delivery of bioactive agents and MMGD. In one embodiment, MMGD is specifically gene-directed enzyme prodrug therapy (GDEPT). This embodiment may be used to enhance the efficacy of GDEPT while reducing toxicity and the need for multiple injections of both the virus and the drug, ultimately enhancing therapeutic outcomes and patient compliance. Recombinant techniques are used to produce the polymers which provide precise control over the structure of the polymers and the incorporation of proteolytic cleavage sites into the polymers. This design improves delivery of bioactive agents when the bioactive agent-loaded polymer is injected into a tissue that displays significant expression of one or more of the relevant proteases.

With regard to the recombinant technique of producing the polymers, disclosed herein is a method to solve the problems of chemical synthetic techniques and natural polymers, in part, by utilizing a genetically engineered protein polymer. Broadly, the creation of the necessary genetic material to produce a genetically engineered protein-based polymer requires the following progression: The creation of a monomer gene, encoding for a single repeat of the desired material, followed by the "polymerization" of this monomer gene to produce a large piece of DNA encoding for the entire polymer. Depending on the synthetic strategy, the polymerization occurs in an expression vector, or the "polymer gene" is digested out of a cloning vector and ligated in to an expression vector, which is transformed into a production organism and grown to high density. Protein production is induced during this growth. Purification of the newly synthesized protein can occur by various methods, but commonly by affinity chromatography or specific phase transitioning at a small laboratory scale. The culture expansion and protein purification procedures are usually system-specific. The polymer gene synthesis may be accomplished by a variety of methods including, but not limited to, random concatamerization, recursive directional ligation, and overlap extension rolling circle amplification (OERCA), all of which are known to those in the relevant art.

Much of the work done in genetically engineered protein polymers has been in the areas of elastin-like polypeptides (ELPs), silk-like protein polymers of both silkworm and spider dragline silks, collagen, and silk-elastin-like polymers (SELPs). Elastin-like protein polymers are generally defined by a repeating sequence of VPGXG (SEQ ID NO: 1), where X is referred to as the "guest residue" and can be any amino acid other than proline. There are two distinct forms of silk produced in nature, coming from spider dragline or the common silkworm, *Bombyx mori*. The primary structure of silkworm silk is dominated by repeats of the hexapeptide GAGAGS (SEQ ID NO: 2), which self-assemble into β-sheet type structures when produced as a linear polymer. Spider dragline silk most commonly used in research applications is derived from *Nephila clavipes*, an orb weaver spider. *N. lavipes* dragline is composed of two different but structurally similar proteins, which are both used to form the natural dragline. The first successful cloning and expression of these two proteins as a genetically engineered protein polymer was based on a consensus repeat sequence derived from the amino acid sequences of each of the proteins. These two consensus sequences were determined to be GQGGYGGLGGQGAGRGGLGGQ GAGA $(A_n)$GGA (SEQ ID NO: 3) for the first discovered, termed NCMAG1 or Spidroin 1, and GPGGYGPGQQGPGGYG-PGQQGPSGPS$(A_n)$ (SEQ ID NO: 4) for NCMAG2, or Spidroin 2.

In one embodiment disclosed herein, the protein polymer is a silk-elastin-like protein polymer (SELP). SELPs are a class of genetically engineered polymers which have been investigated for use in several different applications, including viral gene delivery. This material is composed of repeating units of silk (GAGAGS) (SEQ ID NO: 2) and elastin (GVGVP) (SEQ ID NO: 5) units, which are arranged into blocks of several of each type of unit to form SELP monomers.

Silk-elastin-like polymers are made up of repeating "blocks" of amino acids, referred to as "silk blocks" (Gly-Ala-Gly-Ala-Gly-Ser) (SEQ ID NO: 2) and "elastin blocks" (Gly-Val-Gly-Val-Pro) (SEQ ID NO: 5). The silk blocks consist of the sequence GAGAGS, and are based on the naturally occurring fibrillar silk of $b.$ $mori$, the common silkworm. The design of the elastin blocks is based on mammalian elastin, a very common connective tissue in the body which gives skin its elasticity. A significant body of research has been focused on manipulating the "guest residue" identity of the elastin blocks, and changing the silk: elastin ratio and sequence, to observe how modifications to the structure of SELP affect its properties. In the present disclosure, the repeating blocks of silk and elastin are modified to improve SELP design for bioactive agent delivery in response to overexpression of endogenous proteases, such as for adenoviral gene delivery to solid tumors that overexpress MMP enzymes. Different SELPs that did not include MMP-responsive sequences were studied as described in detail below. Of those studied, SELP815K was most optimal with regard to safety, efficacy, and biodistribution of adenoviral delivery. However, one of skill in the art will understand that SELP815K is one embodiment of the protein polymers according to the present disclosure that may be engineered to include protease cleavage sites and used for delivery of bioactive agents according to the present disclosure. The techniques described herein may further be used to prepare and evaluate other SELPs for other delivery applications.

This disclosure also provides a method to further improve the gene delivery capability of SELPs or other polymers by adding an enzyme-responsive peptide sequence to the monomer unit. In one embodiment, these cleavage sites are matrix metalloproteanase (MMP) cleavage sites.

MMPs are a family of structurally related endopeptidases, which exist in a dynamic balance with tissue inhibitors of metalloproteases (TIMPs) to control myriad biological functions requiring ECM degradation. Proper function and regulation of MMPs is responsible for diverse biological functions such as angiogenesis, embryonic development, and wound healing. There are over 20 known specific MMPs, divided into subgroups based on their additional domains and known biological functions. The main classes of MMPs are collagenases, gelatinases, stromelysins, matrilysins, membrane-type MMPs, and other unclassified MMPs.

MMPs-2 and -9 are known as gelatinase type A and B, respectively, due to their known ability to degrade gelatin (denatured collagen). In normal situations, MMPs-2 and -9 contribute to many processes involving cell migration and signaling, for example angiogenesis and inflammation/innate immunity. However, these MMPs have also been shown to be overexpressed in certain disease states relative to their expression in healthy tissue. The expression and activity of MMPs are increased in almost every type of human cancer, and this correlates with advanced tumor stage, increased invasion and metastasis, and shortened survival. For example, both MMP-2 and MMP-9 are significantly overexpressed in and around primary head and neck squamous cell carcinoma (HNSCC) tumors compared to normal healthy tissues. During metastasis, cancer cells must cross several extracellular matrix barriers. First, they cross the epithelial basement membrane and invade the surrounding stroma, and then they enter blood vessels or lymphatics, extravasate and establish new proliferating colonies.

Experimental evidence for the role of MMPs in in vivo xenograft models shows that the number of colonies formed is reduced by down regulation of MMP-9 and is also reduced in the MMP-2 and MMP-9-null mice as compared with wild type mice. Furthermore, MMP-2 and MMP-9 are strongly implicated in angiogenesis, a necessary event in cancer progression and inflammation.

FIG. 1 illustrates an embodiment of the disclosure where delivery of bioactive agents can be accomplished with MMP-responsive protein polymer sequences in the context of a gene delivery enzyme prodrug therapy (GDEPT) regimen. The protein polymer is designed with MMP cleavage sites at specific locations. The inclusion of MMP-degradable motifs increases degradability of the SELPs and allows a more complete release of viruses from the hydrogels. In some exemplary embodiments, MMP responsive sequences are placed at precise locations in the SELP backbone. In specific examples, these MMP-responsive sequences are placed in the middle or at the ends of the elastin blocks near silk blocks to enable correlation of structure with function (gelation, degradation, release, etc.). In one such embodiment, a prodrug, ganciclovir (GCV) is attached to the polymeric backbone via an MMP responsive sequence. This design results in superior activity and reduced toxicity. These factors combined further enhance the efficacy of SELP-mediated GDEPT. Alternatively, GCV may be included in the protein polymer solution or incorporated in micellar forms to allow controlled release of the drug. In other embodiments, the therapeutic may be another compound such as an anticoagulant or other chemotherapeutic molecule, or combinations thereof.

In addition to SELPs, other protein polymer hydrogels that originate from a variety of sources or combination of sources may be engineered to include protease responsive degradation sites. Examples of proteins that may be used to make protein polymers and copolymers include silk (spider or silkworm), elastin, collagen, (fibrillar, hyaline, matrix-type) keratin, laminin, fibronectin, mucin, aggrecan, and fibrinogen. These, along with combination block copolymers of these protein polymers, all possess the ability to form hydrogels and are within the scope of the present disclosure. By incorporating a domain responsive to targeted proteolytic degradation, the protein polymers may be designed to release their cargo at a desired site. Domains of each protein polymer may be determined based on the role of the protein, such as fibrillar vs hyaline cartilage.

In addition to MMP-2 and -9 cleavage sites, other protease cleavage sites may be incorporated in the protein polymer (see Table 1). Protease-specific sites can be chosen to target a specific response in the desired microenvironment. The reorganization which occurs during wound healing, if predicted to be a normal response, will use known enzymes during various stages. The breakdown of the matrix will react to the enzymes released during a particular stage to have the most beneficial effect. This includes incorporation of specifically recognized cleavage sites for particular MMPs and other proteases. Sequences that are cleaved by specific enzymes used for extracellular matrix remodeling can be optimized to result in the release and degradation of recombinant protein hydrogels based on site preferences. The sequence will depend on the MMP or other proteases, regardless of the protein polymer used, and may be inserted in an advantageous location within the protein polymer.

TABLE 1

MMP Substrates and Cleavage Sequences

| Substrate | Cleavage Sequence | SEQ ID NO: |
|---|---|---|
| MMP-1, -8 (collagenases) | | |
| Type I collagen | APGQIAGQ | SEQ ID NO: 6 |
| Type II collagen | GPQGLAGQ | SEQ ID NO: 7 |
| Type III collagen | GPLGIAGI | SEQ ID NO: 8 |
| Aggrecan | IPENFFGV | SEQ ID NO: 9 |
| MMP-3 (stromelysins) | | |
| Type IX collagen | MAASAKRE | SEQ ID NO: 12 |
| Fibronectin | PFSPLVAT | SEQ ID NO: 13 |
| MMP-2, 9 (gelatinases) | | |
| Type IV collagen | GPQGIFGQ | SEQ ID NO: 10 |
| Cartilage link protein | RAIHIQAE | SEQ ID NO: 11 |
| MMP-7 (matrilysin) | | |
| Laminin | GPLGIAGQ | SEQ ID NO: 14 |
| Elastin | GPQAIAGQ | SEQ ID NO: 15 |

The protein polymer used in the rationale described in FIG. 1 and other embodiments are liquid at temperatures below 37° C. and adenovirus particles are added to the solution. The liquid is injected into the tissue and forms a hydrogel at 37° C. Endogenous MMPs from the tissue cleave the MMP cleavage sites in the protein polymer, resulting in a controlled release of the virus particles and the prodrug. The virus codes for an enzyme that converts the prodrug to its active form. Alternatively, the polynucleotide may express the therapeutic agent itself, such as a growth factor or other therapeutic peptide. The active compound in this embodiment, GCV, is then free to act on the transduced tissue in a localized manner. In other embodiments the protein polymers may be linear and not form hydrogels where incorporation of MMP responsive sequences can facilitate release of complexed or conjugated bioactive agents.

Various embodiments of the disclosed protein polymer are within the scope of this disclosure. In one such embodiment, the protein polymer is a silk-elastin-like protein polymer (SELP) that is produced using recombinant methods and which includes one or more MMP cleavage sites. The recombinant SELP may comprise the structure of SELP815K, including one or more MMP cleavage sites. While the protease cleavage sites may be designed to be cleaved by any protease depending on the type of protease that is expressed in the target tissue, in some embodiments, the enzymatic cleavage site is one that may be cleaved by MMP-2, MMP-9, or both MMP-2 and MMP-9. MMP cleavage sites in the backbone of the polymer may be at various locations in the polymer backbone, such as, in some examples, in the middle of elastin blocks, in the middle of silk blocks, adjacent to silk and elastin junctions, or near the lysine residues in the elastin blocks of each monomer sequence. Recombinant techniques enable such precise localization whereas traditional methods of polymer synthesis produce polymers that do not have a well-defined sequence, and hence do not allow incorporation of MMP responsive sequences in the precise locations of the polymer backbone.

An exemplary embodiment of the copolymer of this disclosure is a copolymer that comprises the following structure, with the MMP-responsive sequence indicated by bold font:

(SEQ ID NO: 16)
[GAGS(GAGAGS)$_2$(GVGVP)$_3$GVGGPQGIFGQPGKGVP(GVGVP)$_{11}$ (GAGAGS)$_5$GA]$_6$.

The copolymer according to this disclosure may form the backbone of a matrix that comprises a drug delivery system for controlled, effective, and safe delivery of bioactive agents to a localized tissue environment. The drug delivery system may include a protein polymer produced using recombinant methods that includes one or more enzymatic cleavage sites and a polynucleotide that encodes an enzyme that converts a prodrug to a therapeutically active compound.

In one set of systems of the disclosure, the drug delivery system comprises a SELP copolymer comprising MMP cleavage sites. The copolymer in the drug delivery system may comprise the structure SELP815K. The one or more MMP cleavage sites in the SELP815K protein polymer may comprise a cleavage site of MMP-2, MMP-9, or both MMP-2 and MMP-9. In some embodiments of the drug delivery system, the copolymer comprises the following structure with the MMP-responsive sequence indicated by bold font:

(SEQ ID NO: 16.)
[GAGS(GAGAGS)$_2$(GVGVP)$_3$GVGGPQGIFGQPGKGVP(GVGVP)$_{11}$ (GAGAGS)$_5$GA]$_6$

The drug delivery system may also include a prodrug. This prodrug may be provided in a solution comprising the copolymer and a polynucleotide that encodes for an enzyme capable of activating the prodrug. Alternatively, the prodrug may be administered separately from the copolymer and polynucleotide. In some systems of the disclosure, the prodrug is GCV.

The drug delivery system may include a polynucleotide that expresses an enzyme capable of converting a prodrug to its active form. In some embodiments, the polynucleotide is an adenovirus. In one embodiment, the adenovirus expresses the enzyme thymidine kinase from the Herpes Simplex Virus. This enzyme may be expressed when the prodrug is GCV as it can activate the prodrug through phosphorylation.

Alternatively, the polynucleotide may express the therapeutic agent itself, such as a growth factor or other therapeutic peptide. In other embodiments, the drug delivery system includes a therapeutic agent within the protein polymer that is a small or large molecule therapeutic, rather than a polynucleotide that expresses a therapeutic agent.

The disclosure also provides a method of using the drug delivery system to deliver a therapeutic. Some methods of delivery may include the following steps: (1) synthesizing a protein polymer comprising MMP cleavage sites using recombinant techniques, (2) maintaining the protein polymer in a liquid form resulting in a protein polymer solution, (3) mixing a bioactive compound into the protein polymer solution, and (4) injecting the solution into the tissue. The bioactive compound may be mixed into the copolymer/polymer solution, attached to the polymeric backbone via an MMP responsive sequence, included in the protein polymer solution, or incorporated in micellar or particle forms to allow controlled release of the bioactive compound. In other embodiments, the method enables the user to deliver to a tissue an enzyme that converts a prodrug to a therapeutically active compound. The method may include the following steps: (1) synthesizing a protein polymer comprising MMP cleavage sites using recombinant techniques, (2) maintaining the protein polymer in a liquid form resulting in a protein polymer solution, (3) mixing a polynucleotide that encodes an enzyme that converts a prodrug to a therapeutically active compound into the protein polymer solution, (4) injecting the solution into the tissue; and (5) administering the prodrug to the tissue. The prodrug may be mixed into the copolymer/polymer solution, attached to the polymeric backbone via an MMP responsive sequence, included in the protein polymer solution, or incorporated in micellar or particle forms to allow controlled release of the prodrug from the polymer matrix. Alternatively, the prodrug may be administered separately to the tissue or the subject.

In one set of embodiments, the method includes the step of synthesizing a copolymer that comprises the structure SELP815K. Such methods may include the step of synthesizing a SELP815K copolymer that includes one or more MMP cleavage sites that are cleavable by MMP-2, MMP-9, or both MMP-2 and MMP-9. These methods may include the step of synthesizing a copolymer that comprises the following structure with the MMP-responsive sequence indicated by bold font:

(SEQ ID NO: 16)
[GAGS(GAGAGS)$_2$(GVGVP)$_3$GVGGPQGIFGQPGKGVP(GVGVP)$_{11}$ (GAGAGS)$_5$GA]$_6$.

In other embodiments, the bioactive compound is a polynucleotide that is mixed in the polymer solution, and comprises an adenovirus. The adenovirus may express herpes simplex virus thymidine kinase (HSV-tk). In these embodiments, the prodrug provided as a step in the method may be GCV which is activated by HSV-tk. In other embodiments, the polynucleotide may express the therapeutic agent itself, such as a growth factor or other therapeutic peptide.

The disclosed system may be used to treat pathologies in a variety of tissues that express excessive levels of proteases, such as MMPs, relative to normal tissues. Target tissues may be either soft tissues or hard tissues. Because the expression and activity of MMPs are increased in almost every type of human cancer, this method may be used to treat nearly every type of cancer. This system may also be used to treat cancers in non-human subjects that express excessive MMPs relative to healthy tissues.

In one embodiment, this system is used to treat primary head and neck squamous cell carcinoma (HNSCC) tumors. In other embodiments, the system may be used to treat osteosarcomas or cancers of the colon, breast, prostate, lung, bladder, brain, or pancreas.

The method may also be used to enhance wound healing because wounded tissue displays increased MMP expression relative to unwounded tissue. Such wounds may be a skin wound, damaged internal tissue, or any other wounded tissue that expresses increased MMP relative to adjacent healthy tissue. The wound may be that which has occurred due to an injury, injection, transcutaneous transplantation, internal hemorrhages or contusions, a disease process, or a surgical procedure.

Organ and tissue transplants, where integration with the host's native tissues is desirable, may benefit from factors released at the transplant site using the drug delivery system as disclosed herein. Anastomoses required to integrate the tissues will show improved healing with the proper release and structural support from injected, degradable hydrogels as disclosed herein.

The disclosed system may also be used in cosmetic enhancement and reconstructive functional sites where environmentally responsive factors will enable tailored release from the protein polymers to result in a desired response. Furthermore, the subject matter disclosed herein may be used as part of prophylactic or corrective measures at or near sites predisposed to disease or unnatural development, such as in joints susceptible to or suffering from arthritis.

The disclosure includes a method of using recombinant techniques to manufacture a silk-elastin-like copolymer comprising one or more MMP cleavage sites. The recombinant method provides control over the precise structure of the protein polymer. This is important because the physicochemical properties of the protein polymer vary with its structure. In some embodiments, the method comprises steps for the manufacture of a SELP815K copolymer that includes one or more sites that may be cleaved by MMP-2, MMP-9, or both MMP-2 and MMP-9. In some embodiments, the method of manufacture creates a protein copolymer that comprises the following structure with the MMP-responsive sequence indicated by bold font:

(SEQ ID NO: 16)
[GAGS(GAGAGS)$_2$(GVGVP)$_3$GVGGPQGIFGQPGKGVP(GVGVP)$_{11}$ (GAGAGS)$_5$GA]$_6$.

The disclosure also describes a kit that may provide the components of the drug delivery system that may be used to administer a therapeutic agent to a tissue. The kit may comprise a protein polymer, such as a silk-elastin-like copolymer that includes MMP cleavage sites. As described elsewhere herein, the copolymer is produced using recombinant methods. The kit also may include an agent comprising a polynucleotide that encodes an enzyme that converts a prodrug to a therapeutically active compound; and a prodrug. Alternatively, the polynucleotide may express or comprise the therapeutic agent itself, such as a growth factor or other therapeutic peptide. The prodrug may be provided in the mixture of protein polymer and polynucleotide or as a separate component. The prodrug may be in liquid form or provided as a freeze dried or lyophilized powder along with a vial or ampoule of sterile water for reconstitution. Similarly, the mixture of protein polymer and polynucleotide may be provided in liquid form or provided as a freeze dried or lyophilized powder along with a vial or ampoule of sterile water for reconstitution.

EXAMPLES

Materials and Methods
Materials

SELP analogs were biosynthesized and characterized according to methods known in the art. Replication defective human adenoviruses (Ad) Type 5 with E1/E3 deletion, under the control of the CMV promoter, encoding for either β-galactosidase (β-gal) or firefly luciferase (Luc) reporter genes were purchased from Vector Biolabs (Philadelphia, Pa., USA). JHU-022 oral cavity cancer cell line was a kind gift from Professor David Sidransky of Johns Hopkins University (Baltimore, Md., USA). Human Leukocyte Elastase was purchased from Elastin Products Company (Owensville, Mo.) and solubilized in Phosphate Buffered Saline (Sigma Aldrich, St. Louis, Mo.). Bicinchoninic acid protein assay was purchased from Thermo Scientific (Waltham, Mass., USA) and the optical density (OD) measurements were performed using the SpectraMax M2 micro plate reader from Molecular Devices (Sunny Vale, Calif., USA) coupled with Softmax analytic software package. For bioluminescent imaging studies, luciferin was obtained from Gold Biotech (St. Louis, Mo., USA). Animals were evaluated for luciferase expression using a Xenogen IVIS100 bioluminescent imaging system from Caliper Life Sciences (Hopkinton, Mass., USA) coupled with analytical software, Igor PRO v.2.2.0, Wavemetrics Inc. (Lake Oswego, Oreg., USA). For establishing xenografts JHU-022 cells were cultured in Advanced Roswell Park Memorial Institute (RPMI 1640) medium containing 2 mM L-Glutamine and 10% fetal calf serum (Gibco, Carlsbad, Calif., USA). Chlorophenol Red-β-D-Galactopyranoside (CPRG) β-gal quantitative kit was purchased from Imgenex (San Diego, Calif., USA). β-Galactosidase Reporter Gene Staining Kit was purchased from Sigma-Aldrich, Inc. (St. Louis, Mo., USA). Luciferase assay system was purchased from Promega (Madison, Wis., USA). Six week old female athymic (nu/nu) mice were purchased from Charles River Laboratories (Davis, Calif., USA) and were used for the animal studies in accordance with the Institutional Animal Care and Use Committee (IACUC) protocol of the University of Utah. Immunocompetent mice were 4-6 week old female standard CD-1 mice, purchased from Charles River Laboratories (Boston, Mass.). CD-1 mice have an intact immune system, which was anticipated to show adverse reactions to the viral vectors comparable to those observed in human trials.

Restriction endonuclease enzymes Ban I, Ban II, BamH I and EcoR V, T4 DNA Ligase and alternative restriction enzymes as needed were purchased from New England Biolab (Beverly, Mass.). DNA ladder and Shrimp alkaline phosphatase (SAP) was purchased from Fermentas (Hanover, Md.). QIAprep Spin Miniprep kits, QIAGEN Plasmid Maxi kits and QiaQuick Gel Extraction kits were obtained from Qiagen (Valencia, Calif.). E. coli HB101 competent cells were purchased from Promega (Madison, Wis.). The cloning and expression vectors, pPT340, pSY1378 and pPT317 were obtained from Protein Polymer Technology, Inc., (San Diego, Calif.), propagated in E. coli HB101, and purified using a Qiagen Giga Kit according to manufacturer's instructions. The concentration and purity of the plasmids were obtained using Ultrospec 4000 (Amersham Biosciences, Piscataway, N.J.) at 260 and 280 nm. Plasmids with $A_{260}/A_{280}$ ratio in the range of 1.8 to 2.0 were used. Plasmids were electrophoresed on a 0.9% agarose gel and stained with ethidium bromide to verify the absence of genomic DNA and the integrity of the plasmid. All other reagents and chemicals were purchased from Sigma-Aldrich or as stated otherwise.

Methods

Quantitative Evaluation of Viral Gene Expression In Vivo

Head and neck cancer xenografts were established by subcutaneously injecting $2\times10^6$ JHU-022 cells suspended in 200 µl Phosphate Buffer Saline (PBS) bilaterally in the flank of athymic nude (nu/nu) mice. Tumors were allowed to grow for two weeks to reach an average diameter of 7 mm. A dose of $5\times10^8$ PFU of Ad-CMV-LacZ was administered to mice with SELP415K (10.8 wt %), SELP47K (8 wt % and 10.8 wt %), SELP815K (4 wt %, 8 wt %, and 10.8 wt %) or physiological saline. Virus-polymer solutions were prepared by thawing SELP and virus stocks and mixing them gently with physiological saline. Mice were anesthetized using 4 wt % isofluorane mixed with oxygen, and intratumorally injected with 25 µl of the polymer-virus solutions using a Hamilton syringe. Mice were euthanized on days 7, 14, and 21 and tumor and liver tissue were isolated. CPRG β-gal colorimetric assays were performed as described previously in the scientific literature. Briefly, fresh tissue samples from the tumor and liver of animals were collected, snap-frozen in liquid nitrogen, ground with mortar and pestle, re-suspended in 1 mL lysis buffer (50 mM HEPES, 5 mM CHAPS, pH 7.4) followed by sonication on ice in 10-15 second bursts for a total of one minute. Recovered tissue lysates were then centrifuged for 45 minutes at 14,000 rpm and, subsequently, upper aqueous layers were used for β-gal quantification. Colorimetric assays were then performed according to the protocol provided with the kit. The optical density (OD) dynamic study was performed to assay the enzyme substrate kinetics, and time point of measurements were set at 40 minutes for tumor β-gal expression and 110 minutes for liver expression. These time points represent the time points of peak interactions for each tissue.

Tumor Histology

For spatial distribution of β-gal in tumors, tissues were cryo-sectioned at 5 µm and stained with a β-gal reporter gene staining kit. Kit manufacturer instructions were modified as follows: tissue sections were fixed for 3 minutes in fixation buffer and then rinsed twice with PBS. Fixed sections were then stained with staining solution for 24 hours at 37° C., rinsed with PBS and observed under light microscope. X-Gal stains β-galactosidase expressing cells and tissue areas dark blue.

Bioluminescence Imaging of Gene Expression In Vivo

Bioluminescence imaging was used as a secondary method of assessment of spatial control over gene expression in JHU-022 tumor-bearing athymic nu/nu mice as established above. Tumors were then injected with 25 µl of SELP415K (10.8 wt %), SELP47K (4 wt %, 8 wt % and 10.8 wt %), SELP815K (4 wt %, 8 wt %, and 10.8 wt %) or physiological saline containing $5\times10^8$ PFU of Ad.CMV.Luc. Imaging was performed on days 4, 7, 10, 14, and 21 by injection with 200 µl of 15 mg/ml luciferin intraperitoneally. Luminescence was imaged after 30 minutes, using Xenogen IVIS100, and images were analyzed using IgorPRO v.2.2.0.

In Vitro Assessment of Hydrogel Degradation

SELP hydrogels (50 µl) were made by drawing 250 µl of 12 wt % SELP47K, SELP415K, and SELP815K, and 8 wt % SELP815K solutions into separate 1 ml syringes. Syringes were placed in a 37° C. incubator and allowed to gel for 24 hours. After incubation, the ends were cut off of each syringe and 50 µl gel disks were cut from the 250 µl cylinder. These gels were placed in the inner wells of a 48-well plate containing 800 µl of PBS+elastase, with a 1:6 dilution curve of elastase starting at 1000 ng/ml. The empty wells of the plate were filled with 1.5 ml PBS to control evaporation, and then the plates were sealed with self-adhesive sealing foil and agitated at 120 RPM. At each time point (1, 3, 7, 10, 14, 17, 21, 24, and 28 days) the full sample volume of 800 µl was removed from each well, placed in a separate 1.5 ml microcentrifuge tube, and stored at −80° C. In order to assess the degradation of the SELPs, the micro BCA protein assay was used according to manufacturer's instructions to measure the soluble protein for each sample, followed by measuring absorbance at 561 nm.

Injection of Therapeutic Ad.HSVtk

For the toxicity studies, Ad.HSVtk was prepared by dilution in either sterile 0.9% physiological saline for injection (Baxter, Deerfield, Ill.) or SELP815K which was previously synthesized to a final concentration of $1.5\times10^{11}$ PFU of virus per ml of solution. SELP815K was used at a final concentration of 4 wt %. Mice were anesthetized and maintained under anesthesia with 3% isofluorane in oxygen. After shaving and cleaning the injection site with 60% isopropanol, mice were subcutaneously injected in the right flank with 50 µl of solution using a 250 µl Hamilton syringe with a 26G needle. This resulted in an actual viral titer of ~7.6×10$^9$ PFU administered per mouse. The injection site was gently clamped for 10 seconds to prevent leakage, after which mice were returned to their cages. For consistency, the day of viral injection was defined as day 0.

Injection of Ganciclovir (GCV)

For treatment groups, a suspension of 1 mg GCV (Sigma Aldrich, St. Louis, Mo.) per ml of 0.9% physiological saline was prepared and sterilized through a 0.22 µm filter. Each day, animal weights were recorded, injection sites cleaned with 60% isopropanol, and mice injected i.p. with 1 mg/ml GCV suspension through a 26G needle sufficient for a total dose of 25 mg/kg body weight. Average dosing volume for these studies was approximately 0.6 ml. Mice were injected daily for the first four weeks of the 12 week recovery study, and for the entirety of the 1, 2, and 4 week studies.

Necropsy and Data Collection

Upon completion of each study, mice were individually euthanized using 70% $CO_2$ in oxygen, with euthanasia confirmed by lack of breathing for 10 seconds. Blood was taken via inferior vena cava stick, and drawn into a heparinized syringe through a 25G needle and deposited into a heparinized plastic blood tube. Minimal evidence of hemolysis was observed in blood samples. Injection sites were dissected for visual observation of local inflammation. Complete blood counts (CBCs) were performed within 2 hours of blood sample collection using a CBC-DIFF (Heska, Loveland, Colo.) blood count analyzer. Following CBC, samples were centrifuged at 10,000 rpm for 2.5 minutes and rapidly frozen at −80° C. for future analysis.

TABLE 2

Animals per study group and end points for toxicity studies

| Group | 1 week | 2 weeks | 4 weeks | 12 weeks |
|---|---|---|---|---|
| Control (saline only) | 3 | 9 | 9 | 3 |
| Ad.HSVtk + GCV | 4 | 9 | 9 | 4 |
| SELP-815K 4% + Ad.HSVtk + GCV | 4 | 9 | 9 | 4 |

Construction of the SELP815K-MMPRS Monomer Gene Segment

Plasmid pSY1378 (cloning vector) was digested with BanI and dephosphorylated with shrimp alkaline phosphatase (SAP). Plasmid pPT317 containing two copies of SELP815K monomer gene segment were digested with BanI and separated on a 1% agarose gel. The ~400 bp fragment corresponding to SELP815K monomer gene was purified using the Qiaquick Gel Extraction Kit. SELP815K monomer gene segments were ligated with linearized, dephosphorylated pSY1378 in a 3:1 ratio overnight at room temperature. The ligation mixture was used to transform MAXefficiency Dh5α *E. coli* and the transformation was plated on chloramphenicol-selective LB agar plates. Cultures were grown overnight and colonies were selected and grown in 4 ml starter cultures in chloramphenicol-selective Terrific Broth overnight at 37° C. in a shaking incubator at 240 RPM. DNA was isolated from cultures by Qiaprep Spin Miniprep kit, and screened by digestion with BanI. A positive colony was then grown overnight in a 200 ml chloramphenicol-selective Terrific Broth culture and DNA was then extracted using a Qiagen Maxiprep kit.

Custom oligonucleotides encoding for the MMP-responsive sequence GPQGIFGQ (SEQ ID NO: 10) in addition to XgaI-compatible overhangs and 5' phosphorylation were solubilized in annealing buffer composed of 10 mM Tris, 50 mM NaCl, and 1 mM EDTA in 18 MΩ deionized water to a concentration of 1 mM. The sequences of the oligomers are as follows:

```
FWD:
                                     (SEQ ID NO: 17)
5' AGGACCGCAAGGAATTTTTGGACA GCCTGG 3'
(5' Phosphorylated)

REV:
                                     (SEQ ID NO: 18)
5' TCCAGGCTGTCCAAAAATTCCTTGCGGTCC 3'
(5' Phosphorylated)
```

Oligomers were mixed in a 1:1 ratio and 50 µl of oligomer mixture was annealed by heating to 95° C. in an aluminum heating block, then allowed to cool to room temperature gradually by switching off the heating block.

Plasmid pSY1378 containing SELP815K monomer gene segment was digested with XagI and dephosphorylated using SAP. Annealed oligomers were ligated with the linearized pSY1378+SELP815K monomer gene segment in a 5:1 molar ratio overnight at room temperature. This ligation mixture was used to transform MAXefficiency Dh5α *E. coli* and the transformation was plated on chloramphenicol-selective LB agar plates and grown overnight at 37° C. Colonies were grown in 4 ml chloramphenicol-selective overnight Terrific Broth cultures, DNA extracted, and digested with AvaII to identify colonies containing the MMP-responsive insert, which appeared as a 311 bp fragment on an agarose gel. DNA sequencing was used to confirm correct insertion, after which 200 ml terrific broth cultures were grown and pSY1378 containing SELP815K-MMPRS monomer gene segment was isolated using a Qiagen Maxiprep kit.

Construction of the SELP815K-MMPRS Polymer Gene Segment

Plasmid pPT317 (expression plasmid) containing SELP815K dimer was digested with BanI and dephosphorylated using SAP. pSY1378 containing SELP815K-MMPRS monomer gene segment was digested with BanI. Both digests were separated on a 1% agarose gel. The bands corresponding to the 4000 bp linearized and dephosphorylated pPT317 parental vector and the ~400 bp band corresponding to SELP815K-MMPRS monomer gene segment were purified. Monomer gene segments and linearized dephosphorylated pPT317 were ligated overnight at room temperature at a 42.5:1 molar ratio, with total DNA content of ~650 ng. The ligation mixture was used to transform MAXefficiency Dh5α *E. coli* and the transformation was plated on kanamycin-selective LB agar plates and grown overnight at 30° C. Colonies were grown in kanamycin-selective Terrific Broth, DNA extracted with Qiagen Minipreps, and screened with a double digest with NcoI and XcmI. Screening digests were run on 1% agarose and colonies displaying a band at ~2400 bp, corresponding to SELP815K-MMPRS 6-mer were stocked in 50% glycerol and analyzed for protein production.

Small-Scale Protein Production by SELP815K-MMPRS

The ability of the newly constructed polymer gene containing plasmid pPT317 to induce protein production was confirmed by transforming the genetically engineered EC3R *E. coli* with pPT317 encoding SELP815K-MMPRS 6-mer. 6-mer was chosen specifically because it most accurately mimics the molecular weight of previous SELP constructs for hydrogel formation, including SELP815K. EC3R was derived from a post-fermentation cell culture of pPT317+ SELP815K 6-mer by defrosting a small chip of post-fermentation cell mass which was grown using the production cell line EC3 from Protein Polymer Technologies, Inc. (San Diego, Calif.). Approximately 25 subculture/replica plate cycles were performed on cells from this culture until a viable kanamycin-sensitive *E. coli* colony was identified, indicating that the plasmid encoding SELP815K 6-mer had been purged. Following transformation, colony screening, and identification of a positive colony, a 4 ml kanamycin-selective MM50 culture was inoculated, grown to slightly turbid culture and then divided into two subcultures and diluted to 4 ml each with additional MM50 (Protein Polymer Technologies, Inc. San Diego, Calif.). One of these cultures was intended for protein production, while the other was earmarked for inoculums development. These cultures were grown at 30° C. at 240 RPM agitation until OD600 indicated that the cells were approaching stationary phase. At this point, the inoculum development culture was divided and added to each of two 0.4 L MM50 cultures and grown at 30° C. and 240 RPM, while the culture for protein production capacity was heat shocked and outgrown for analysis. Specifically, the culture was immersed in 60° C. water and culture temperature was monitored until it reached 42° C., at which point it was transferred to a 42° C. water bath for 5 minutes. Following induction, the culture was grown at 40° C. and 240 RPM for 2 hours, at which point protein production was evaluated by SDS-PAGE by comparing the induced culture to a pre-induction sample and a known SELP815K 6-mer sample. Inoculum OD600 was monitored hourly until an OD greater than 4.0 was measured (10 mm path length, Eppendorf BioPhotometer) at which point it was used to inoculate the fermenter.

Large Scale Polymer Production by SELP815K-MMPRS

SELP815K-MMPRS was produced in gram quantities by fermentation in a 14 liter New Brunswick Scientific BioFlo 115 fermenter (Eppendorf, Enfield, Conn.) with a 10 liter working volume. An initial volume of 6 liters of MM50 was added sterile to the autoclaved fermenter, followed by the 0.8 liter inoculum. Fermentation was initiated at 30° C. and 1000 RPM agitation, with 8-10 liters/minute airflow, pH 6.8. Foam was controlled by addition of Antifoam 204 (Sigma Aldrich, St. Louis, Mo.), and was controlled by a foam level probe placed approximately two inches above the culture level. pH control was done by addition of ammonium hydroxide via the fermenter pH control loop. When dissolved oxygen decreased below 60%, agitation was increased to 1200 RPM. Dissolved oxygen was monitored constantly until it was observed to show a sharp drop followed by recovery to nearly 90%, indicating a switch of the bacteria from anabolic to catabolic metabolism (depletion of initial glucose charge), at which point glucose feed was initiated at 150 ml/min.

Culture OD600 was measured every 2 hours until OD600 reached 100, at which point protein production was induced by heat shock. In order to heat shock the culture, the fermenter heating blanket was adjusted to maximum output, and water heated to 80° C. was rapidly pumped through the cooling loop by a peristaltic pump. When temperature reached 41° C., the heating blanket was removed and cold tap water (approximately 10-15° C.) was pumped through the cooling loop briefly to purge the hot water from the system. Temperature reached 42° C. between three and four minutes, with one degree of overshoot. The heating blanket was then replaced, and temperature was allowed to gradually decrease to 40° C., approximately 45 minutes. At this point the cooling system was reconnected, and the temperature set point was adjusted to 40° C.

OD600 was continually monitored following induction, until it was observed to decrease at which point harvest was initiated. Final culture OD600 was 154, with a maximum of 180. Harvest began by removing the heating blanket, stopping glucose feed, and reducing agitation to 300 RPM. Ice-cold water was pumped through the cooling loop until culture temperature reached 10° C., at which point the culture was pumped into 1 liter centrifuge bottles and pelleted at 6000×g for 30 minutes at 4° C. Wet cell paste was stocked in plastic bags, weighed, and frozen at −80° C. to aid in cell lysis for SELP purification. Approximately 2.2 kg of wet cell paste was yielded from fermentation of SELP815K-MMPRS 6-mer.

Purification of SELP815K-MMPRS

Approximately 1.1 kg of frozen cell paste from fermentation was defrosted and lysed via high-pressure mechanical extrusion using a Microfluidics Microfluidizer 110M set to 10,000 psi. The lysed cell solution was then centrifuged at 4° C. for 30 minutes to remove cell debris, and PEI was used to precipitate nucleic acids and other negatively charged contaminants. The PEI-treated supernatant was then centrifuged at 4° C., after which the supernatant was subjected to ammonium sulfate precipitation. The precipitated protein was solubilized and then further purified by both cation and anion exchange chromatography, and tangential flow filtration. Following chromatography and filtration steps, the polymer solution was lyophilized in depyrogenated flasks, transferred to depyrogenated Teflon jars, and stored at −80° C. Yield from a single SELP815K-MMPRS purification batch was approximately 2.5 g.

Polymer Characterization

Characterization of SELP815K-MMPRS polymers was performed by MALDI-TOF mass spectrometry, amino acid composition analysis, SDS-PAGE, and enzymatic digest analysis via HPLC for MMP-2 and MMP-9. MALDI-TOF was performed by the University of Utah Mass Spectrometry and Proteomics core facility, while amino acid analysis was performed by Alphalyse, Inc. (Palo Alto, Calif.).

For SDS-PAGE, samples of lyophilized SELP815K and SELP815K-MMPRS were solubilized in "Reaction Buffer" (RB) containing 50 mM Tris-HCl, 150 mM NaCl, 5 mM $CaCl_2$, and 0.2 mM $NaN_3$, pH 7.6 at a concentration of 1 mg/ml. This buffer recipe is sourced from the Molecular Probes EnzChek Gelatinase/Collagenase Assay Kit (Invitrogen, Carlsbad, Calif.), which was used to confirm the activity of MMP-2 and MMP-9 prior to use. 2× Laemmli Buffer was supplemented with 5% β-mercaptoethanol and added 1:1 by volume to the polymer solutions, which were then placed in a PCR thermal cycler and heated to 95° C. for five minutes to denature the protein. 25 μl of each sample was added to 4-15% Bis-Tris precast PAGE gel and electrophoresis was performed at 200V until the dye front reached the bottom of the gel, approximately 30 minutes. Kaleidoscope protein standard was used as a molecular weight marker. Following electrophoresis, gels were stained with GelCode Blue (colloidal Coomassie formulation) following manufacturer's instructions for staining and destaining.

Enzymatic digest was performed by solubilizing SELP815K and SELP815K-MMPRS in RB at 1 mg/ml. 100 μl samples of each polymer were digested with a final concentration of 10 nM and 40 nM MMP-2 or MMP-9. MMP samples were incubated at room temperature for 2, 4, 12, 24, 36, and 48 hours and samples were run on PAGE gels and stained with GelCode Blue to visualize band patterns corresponding to protein degradation.

Hydrogel Characterization

The properties of hydrogels formed from SELPs are strongly dependent on the shear applied to liquid solutions of polymer prior to gelation. SELPs solubilized in phosphate buffered saline were loaded into a 1 ml luer-lock syringe connected at the hub to another 1 ml luer-lock syringe via two 27G needles, joined by a section of 0.0155" HPLC tubing. The SELP solution was passed through this device at maximum hand pressure for five full bidirectional cycles, at which point it was used for studies.

Hydrogels were characterized for their sensitivity to MMP degradation in the context of protein loss from the gel, changes in mechanical properties, and release of model 100 nm fluorescent nanoparticles. Previous applications of SELP815K have investigated its utility as a viral delivery material, and this particle size was chosen as a model for the adenoviruses. For the protein release and mechanical properties, 10 wt % solutions of SELP815K and SELP815K-MMPRS were sheared according to the above protocol, and then loaded into 1 ml tuberculin slip-tip syringe. Syringes were sealed with Parafilm and allowed to gel upright overnight at 37° C. Following gelation, the end of the syringe was cut off with an autoclaved razor blade and individual 50 µl test samples were cut off of the gel cylinder using a new autoclaved razor blade. Gel samples were placed in round bottom 1.8 ml cryovials with gasket-sealed screw caps, and 250 µl of test solution consisting of RB alone, RB+MMP-2 (10 nM), or RB+MMP-9 (10 nM) was added to each tube. Samples were agitated at 180 RPM at room temperature. Test solution was completely withdrawn every 32-40 hours and frozen at −20° C., rinsed with RB, and replaced. For the release study, gels were formed and treated as above except that when the SELP solutions were being made, 6.6 µl of 0.2% fluorescent bead suspension was added per ml of SELP solution, and all agitation and sample manipulation was performed with minimal light to avoid photobleaching.

Protein loss was quantified using a Modified Lowry Assay Kit, and using known SELP solutions for the standard curve instead of the supplied bovine serum albumin, as SELP contains few Lowry-reactive amino acids. The mechanical properties of SELPs were evaluated in cyclic compression at 1 Hz and 1% strain, with ~10 grams of preloading applied for 10 minutes to eliminate stress relaxation. Stress was measured using a 2 lb load cell. Release was quantified by measuring the fluorescence of release samples with an excitation/emission of 260/515.

Results

Example 1: Synthesis and Characterization of SELP Analogues

The synthesis and characterization of three SELP analogues were carried out as illustrated in FIG. 3. Head and tail sequences as shown in FIG. 2. Silk units are in double underlined (GAGAGS) (SEQ ID NO: 2), elastin units are single underlined (GVGVP) (SEQ ID NO: 5), and lysine-substituted elastin units are underlined with a dashed line (GKGVP) (SEQ ID NO: 23). G=Glycine, A=Alanine, S=Serine, V=Valine, P=Proline, K=Lysine. These structures were designed to have similar molecular weights but varying lengths of silk and elastin repeats within the monomeric unit. SELP47K monomer has 4 silk units, 7 elastin units and an additional elastin unit containing a lysine (K) residue). This monomer was repeated 12 times to give a polymer with molecular weight 69,814 Da. SELP415K monomer has longer elastin units (fifteen) however the monomer is repeated 8 times to give a molecular weight of 71,500 Da similar to SELP47K. SELP815K was designed to have longer silk units compared to SELP47K and SELP415K but similar elastin units compared to SELP415K. This monomer was repeated 6 times (molecular weight 65,374 Da) so that the final molecular weight of the three polymers remained relatively constant. The rationale for the design was that while elastin blocks determine pore size (and ultimately release), silk blocks confer crystallinity, network formation and mechanical properties. SELP815K was created with the intention of producing a SELP polymer with similar mechanical properties and gelation kinetics as SELP47K, with a looser pore structure to allow more complete release of therapeutic adenoviruses for the treatment of solid tumor carcinomas. A typical biosynthesis of the analogs is outlined in FIG. 3. In summary, the SELP415K plasmid pPT340 was digested to produce a SELP215K plasmid (step I). Next, plasmid pSY1378, encoding for six silk units, was linearized (step II) and the portion of pPT340 encoding for SELP215K was ligated with linear pSY1378 (step III), producing a monomer sequence for SELP815K. Monomer gene sequences for SELP815K were then digested out of the pSY1378 (step IV). The expression vector, pPT317, was linearized (step V). Random multimerization was performed with pPT317 and the SELP815K monomer gene segments, producing various SELP815K repeat numbers in the pPT317 expression vector (step VI).

Basic results for the synthesis of one polymer analog (SELP815K) are discussed herein to illustrate the level of control over polymer synthesis using the recombinant technique. Once SELP815K gene segment was synthesized, experiments were performed to confirm the characteristics of the linear molecule. FIG. 4A shows the progression of SELP815K monomer gene segment synthesis via PAGE. Lanes were loaded as follows: lane 1, 1 kb DNA ladder (0.25-10 kDa); lane 2: linearized pSY1378 with SLP-6; lane 3: linearized pSY1378 after SELP-215K insertion; lane 4: BanI digest of pSY1378 after SELP-215K insertion (linearized plasmid and SELP-815K monomer). FIG. 4B shows the formation of the polymer gene segment. Lanes were loaded as follows: lane 1, 1 kb DNA ladder (0.25-10 kDa); lane 2: SELP-815K monomer insert; lane 3: self-ligated SELP-815K monomer mixture (1-mer, 2-mer, 3-mer, up to n-mer). FIG. 4C illustrates the DNA sequence for the SELP815K monomer gene segment in between the two BanI restriction sites, which is the key sequence dictating the amino acid sequence of the monomers in the final polymer. The SELP815K monomer gene segment was constructed from insertion of SELP215K (underlined) inside SLP-6 sequence resulting in a 384 bp segment flanked by BanI recognition sites (highlighted in gray).

The multimer gene segments encoding SELP815K were then cloned, expressed, purified and characterized. Characterization of the SELP proteins was performed using matrix-assisted laser desorption ionization-time of flight mass spectrometry (MALDI-TOF). The MALDI-TOF results (FIG. 5) show equally spaced and decreasing intensity peaks, with the masses consistent with the desired molecular weights of the SELP815K polymers. Several genes for different molecular weight SELP815K were separately (not in a mixture) cloned and expressed. SELP815K-6-mer gene (molecular weight 65,374 Da similar to that of SELP47K and SELP415K) was selected for further large scale fermentation and purification, and hydrogel formation. These results show the presence of several different SELP815K repeat numbers. Single repeat numbers were selected by colony expression and selection, yielding polymer of only one of the displayed molecular weights. Well-established methods were used to confirm the accuracy of the amino acid sequence in SELP, and clearly demonstrate the monodispersity of each of the molecular weight populations, which can be individually selected and expressed. Similar strategies were conducted to synthesize and characterize SELP47K and SELP415K.

Further characterization of linear SELP molecules, including atomic force microscopy (AFM) techniques, were used to evaluate the interactions responsible for network formation. Polymer-polymer interaction for the SELP analogs was influenced by polymer structure and concentration, with lower concentrations showing poor network formation on mica. A typical AFM image of a low, non-hydrogel forming concentration of SELP415K (FIG. 6) shows the formation of polymeric networks. This image illustrate an AFM image of linear SELP415K (1 µg/ml-non hydrogel forming) at NaCl concentrations of 5 mM on mica surface. Specifically, this image illustrates polymer-polymer interaction and network formation of SELPs.

Example 2: Formation and In Vitro Characterization of SELP Hydrogels

Once the three linear polymers were synthesized, expressed, fermented, purified, and characterized, hydrogels were made by incubating aliquots of the polymers at 37° C. The critical gelation concentration (CGC) of the polymers, i.e., the concentration above which a non-flowing gel phase was formed, were evaluated for all polymers. It was observed that, when cured for 4 hours, SELP815K formed hydrogels in the concentration range of 4 wt %-12 wt % similar to SELP47K, whereas, in the case of SELP415K, a minimum of 12 wt % concentration was necessary for gel formation. This is attributed to similar silk to elastin ratio (S:E) in case of SELP47K and 815K allowing the formation of comparable number of silk cross-links per fibril. The lower S:E ratio in the case of SELP415K presents lesser number of hydrogen bonding (silk) sites for formation as compared to the higher silk containing analogs (SELP47K and SELP815K) thereby requiring more polymer chains (or higher CGC) to self-assemble and form robust hydrogels.

Next, extensive studies were performed to examine the swelling characteristics of these hydrogels as a function of polymer structure, concentration and environmental stimuli (pH, ionic strength, temperature). FIGS. 7A-C illustrate the differences in swelling ratio as a function of selected parameters. Swelling ratio (q) is the weight of wet gel divided by dry gel and is often used to gain insight into flexibility and porosity of hydrogel systems. FIG. 7A illustrates the effects of cure time and polymer structure on swelling ratio in Dulbecco's Phosphate Buffered Saline. It is demonstrated that SELP415K possesses the highest swelling ratio during lower cure times, which is expected due to its lower density of silk units and therefore more open pore structure than SELP47K and SELP815K. The longer elastin units of SELP815K are hypothesized to contribute to a more open pore structure than that found in SELP47K, which is shown to some extent in the swelling data. FIGS. 7B and 7C show swelling ratio dependence on ionic strength of release medium and temperature, respectively. The legend for the graphs in FIG. 7 is as follows: 7A,B: White: SELP47K, 12 wt %. Grey: SELP415K 12 wt %. Black: SELP815K 12 wt %. 7C: ▲:SELP47K, ■:SELP815K, and ♦: SELP415K, all at 12 wt %.

An interesting point in this data is that for SELP415K, environmental changes after gel formation appear to have a greater effect than for SELP47K and SELP815K. This is due to a higher occurrence of rigid, crosslink-like structures in the latter systems compared to SELP415K hydrogels, instigated by a higher density of silk blocks as opposed to the more self-assembly dominated structures formed by elastin blocks. The higher sensitivity of the self-assembly processes to environmental conditions compared to the crosslinking processes yields a more sensitive hydrogel as elastin block content increases. This can have potential utility in the context of stimuli-sensitive drug delivery. However, for all intents and purposes, as described in later sections, SELP415K showed poor properties in forming robust hydrogels in vivo and enhancing transfection efficiency in matrix-mediated viral gene delivery. All SELP hydrogels possess a lack of pH sensitivity of swelling ratio in the range studied. Overall the swelling studies pointed to the suitability of SELP47K and SELP815K for subsequent evaluation in matrix-mediated gene delivery.

It was predicted that polymer structure would also play a large role in the mechanical properties of the hydrogels. Dynamic mechanical analysis (DMA) was used to examine hydrogels made from each of the SELP analogues, and as predicted, there was a strong dependence of the results on the silk and elastin content of the polymers, and the arrangement of the silk and elastin blocks. FIG. 8 illustrates DMA of the SELP hydrogels, each at 12 wt % and demonstrates that the final storage moduli of SELP hydrogels is in the order SELP47K>SELP815K>SELP415K. This is opposite the order observed in the swelling studies, which is to be expected assuming the crosslinking density decreases with increasing swelling and decreasing mechanical properties for analogous materials. The legend for the graph shown in FIG. 8 is as follows: triangles: SELP-47K, squares: SELP-815K, diamonds: SELP-415K. Highly controlled structure in SELPs allows fine-tuning of mechanical properties.

To gain further insight into the hydrogel pore structure, network properties were examined as a function of polymer sequence by small angle neutron scattering (SANS) techniques (FIG. 9). SANS allows the examination of microstructures in the range 1-100 nm through the analysis of elastic neutron scattering. SANS analysis was used to examine the correlation between the observed macroscopic properties of SELPs (12% wt), such as equilibrium swelling and mechanical modulus, with the underlying network structure. The SANS scattering curves are shown in FIG. 9. The data was fit using a combined Debye-Bueche power law model which revealed trends in the SELP fibril correlation length that confirm observations about structural effects. SELP hydrogels conformed closely with a modified gel model of the general form $I(Q)=AQ^b+(BQ^2\varepsilon^2)^2+C$, which uses a power-law fit for the high q scattering combined with the Debye-Bueche model at low to intermediate Q (above $Q=0.02$ Å$^{-1}$). The combined Debye-Bueche/power law model provided a nearly complete fit over the full q-range of collected data. This analysis of SELP47K, 415K, and 815K revealed scattering profiles that, while similar in form, showed characteristic trend in low q power-law scattering and Debye-Bueche correlation length $((4\pi K\varepsilon^2 corrL^2)/(1+Q^2 corrL^2)^2)$. The calculated correlation length (Table 3) depicts a trend in the observation that are in the order SELP-415K>SELP-815K>SELP-47K. This is consistent with the DMA data (FIG. 8) showing that SELP-47K had the highest storage modulus. Presence of shorter elastin blocks separating the crystallized silk blocks of the SELP-47K compared with the other analogs (-415K and -815K) resulted in a stiffer hydrogel with smaller spacing of the crystalline silk units. In contrast, SELP-415K had the longest correlation length and the lowest storage modulus. The silk blocks of SELP-415K are separated by elastin blocks twice the length as -47K, and as these cross-linking blocks move further apart, the elastin-like nature of the SELP becomes more pronounced and the storage modulus decreases. SELP-815K presents an interesting case where the silk blocks are doubled in length over SELP-47K while also having a long elastin block as in SELP415K. While the larger silk blocks provide improved cross-linking when combined with a 15-unit elastin block, the correlation length and storage modulus falls between those of SELP47K and 415K. The combination of SANS and DMA data together suggest that the elastin block of the SELPs predominantly influence the effective pore size.

Example 3: In Vitro Adenoviral Release and Degradation of SELPs

Following physicochemical characterization of the hydrogels, their interaction with adenoviruses was examined. This was done to identify what, if any, the ramifications are of loading SELP hydrogels with viruses. These results show that adenovirus incorporation does not affect the swelling ratios of SELP hydrogels. Adenoviruses seem to stabilize the gelation of SELPs, as the virus groups have less

TABLE 3

Debye-Bueche/power law results for SELP hydrogels.

| SELP composition (12 wt %) | Power-law low Q slope | Correlation length from Debye-Bueche$^a$ | Debye-Bueche mid-Q slope |
|---|---|---|---|
| SELP-47K | 2.74 | 4.58 nm ± 0.01 nm | ~-3 |
| SELP-415K | 2.51 | 6.55 nm ± 0.78 nm | ~-3 |
| SELP-815K | 3.26 | 5.94 nm ± 1.18 nm | ~-3 | time-dependent changes in swelling ratio than do the no-virus group, and the effect seems to be virus concentration dependent. An important consideration in adenoviral gene delivery is the bioactivity of viruses over time. We investigated the bioactivity of released adenoviral particles from hydrogels in buffer media. A significant drop in the bioactivity of viruses, measured based on beta-galactosidase expression in cells in vitro, was observed over time (up to 50% drop by day 15 and 75% drop by day 28). Bioactivities of released viruses from polymers were not different or lower than viruses alone. FIG. 10 shows a typical adenoviral release profile from SELP hydrogels in vitro. Consistent with the observed physicochemical properties and structure of hydrogels, SELPs with longer elastin units (415K) and lower concentration (e.g., 4 wt %) released adenoviruses faster than SELPs with shorter elastin units (e.g., 47K) and higher polymer concentration (12 wt %). This experiment revealed the ability to control release as a function of SELP structure and concentration. Release decreased due to higher density of crosslinking in the hydrogels. The legend for FIG. 10 is as follows: ♦4 wt % SELP47K, ▲: 8 wt % SELP47K, ■:11.7 wt % SELP47K, +: 11.7 wt % SELP415K.

Next, studies were conducted to examine the influence of elastase on hydrogel properties, specifically soluble fraction release. These studies showed that SELP hydrogels exhibit sensitivity to elastase, which is found in low quantities intratumorally. Specifically, FIG. 11 shows the time dependence of soluble fraction release for hydrogels composed of all three different SELP structures. Similar to the previous characterizations, SELP415K appears to be the most sensitive to elastase degradation, while SELP815K shows the lowest sensitivity to degradation. Interestingly, SELP815K at 8 wt % is more resistant to degradation than SELP47K and SELP415K at 12 wt %. This result can be explained by the large quantity of silk unit crosslinks which form in SELP815K, versus the lower number of such structures formed in the other two hydrogels. By possessing dense crosslinking in addition to large elastin units, SELP815K is able to resist degradation most effectively while exhibiting intermediate swelling and pore size. The legend for FIG. 11 is as follows: ■: SELP415K 12 wt %, ●: SELP47K 12 wt %, ▲: SELP815K 12 wt %, Δ: SELP815K 8 wt %.

Overall results of physicochemical characterization of hydrogels showed that by controlling the length, sequence and ratio of silk and elastin blocks as well as the concentration of polymers it is possible to control the swelling, modulus of elasticity, pore size, viral release and biodegradation of the hydrogels. Degradation in vitro was suboptimal, and SELP415K formed gels with loose networks. SELP815K had an intermediate modulus with pore sizes larger than SELP47K. Viruses did not influence the network properties of the hydrogels. Release was controlled by length of silk and elastin units and polymer concentration. Bioactivity of the viruses released from the matrices did not decrease compared to free virus in media. In both cases a gradual decrease in bioactivity over 28 days was observed. These studies set the stage for examination of matrix-mediated adenovirus delivery in HNSCC tumor models.

Example 4: Bioluminescent Imaging of SELP-Mediated Gene Expression

Bioluminescent imaging of live tumor-bearing animals allows gene expression to be monitored in the same animal over the study period without the need to sacrifice the mouse for analysis. Unfortunately, issues with light attenuation, scattering, and reflection reduce the value of this technique for quantitative measurement. In this study both methods were used to provide a more comprehensive assessment of gene expression by SELP-mediated delivery of adenoviruses to head and neck tumors. Each animal expressed luciferase in the tumor at day 4, and that expression continues for all animals up to Day 14. Two patches of expression were observed anterior to the tumor which were due to liver expression. Liver expression appeared in only one animal in each group over the course of the study. In the virus only condition, only three animals expressed luciferase at day 4. At day 21, there was still tumor expression in all but one animal in the SELP-mediated group, illustrating the ability of SELP to prolong gene expression compared to free virus injection at the same time point, which shows only one animal with appreciable expression starting on day 14. The bioluminescent images of gene expression correlate with the data acquired through enzyme assay and confirm the influence of SELP on controlling gene expression, which would likely improve the efficacy of treatment of head and neck cancer with a virus/prodrug system. Additionally, based on these results, SELP may improve the safety of this treatment, as SELP causes lower cumulative transfection in the liver, the primary organ affected by adenovirus toxicity.

Example 5: SELP-Mediated Delivery of Adenoviruses to Head and Neck Tumors In Vivo Polymer structures and compositions that formed robust hydrogels were selected for matrix-mediated delivery of reporter genes in a murine model of HNSCC. Extensive studies were performed to examine the ability of SELPs to control delivery of adenoviruses in vivo. Results show prolonged and localized viral transfection in the tumors with minimal evidence of viral gene expression in the liver or other peripheral targets. Nude mice were given subcutaneous xenograft tumors of JHU-022, a HNSCC cell line. Tumors were allowed to grow to a dimension of 7×7 mm before they were injected with either virus only in 50 µl of saline, or virus delivered in 50 µl of SELP. All injections of virus were done using $5\times10^8$ PFU of the recombinant adenovirus, Ad.CMV.LacZ, which codes for β-galactosidase. Animals were sacrificed at days 7, 14, and 21 for analysis of gene expression, and analyzed using a colorimetric tissue lysate assay for β-galactosidase. The results of these studies, shown in FIGS. 12A-C, indicate that SELP-mediated delivery localizes, increases, and prolongs transfection in vivo. FIG. 12A (left) shows gene expression in tumor tissue over the three weeks of the experiment at each condition. It is clear that delivering adenovirus in SELP, specifically SELP815K at 4 wt %, has an advantage over intratumoral injection of free adenovirus. SELP815K displayed more than 50-fold higher transfection at week one compared to free virus, and maintains much higher gene expression levels throughout the course of the experiment. FIG. 12B (center) shows gene expression in the liver for the same animals as FIG. 12A (left). An important advantage of using SELP is shown in FIG. 12C (right), which displays the ratio of tumor to liver expression for each condition. SELP815K at 4 wt % shows a maximum of 55-fold difference in tumor vs. liver transfection at week two, and shows very high tumor transfection levels compared to liver for both weeks 1 and 3.

A visual representation of the typical differences between the SELP groups and the free virus group was obtained by β-galactosidase histological staining of tumor sections. Specifically, the spatial and temporal patterns of β-galactosidase expression in SELP415K, SELP815K, and plain virus treatment groups were evaluated by staining with X-gal of both tumor and liver tissues. It was shown that not only did SELP increase transfection levels compared to free virus, but also prolonged transfection out to at least three weeks, while free virus did not cause detectable levels of transfection at three weeks. Specifically, we performed histological staining for beta-galactosidase in JHU-022 tumors injected with adenovirus delivered in either saline or SELP polymers at week 1 and week 3. These data indicate that SELP hydrogels significantly localize and prolong gene expression in vivo.

In order to fully illustrate the potential of SELP as an injectable, in situ gel forming delivery system for the treatment of HNSCC solid tumors, a study was performed on the efficacy of this system using a GDEPT approach. The system chosen was herpes simplex virus thymidine kinase (HSV-tk) as the enzyme, and ganciclovir (GCV) as the prodrug. To accomplish this, a custom adenoviral construct was designed and used for this study. The construct contained genes which encode for HSV-tk and genes which encode for luciferase, a common reporter enzyme. A map of the adenoviral genome is shown in FIG. 13. This novel construct allowed both efficacy and biodistribution to be assessed simultaneously in vivo. Specifically, by combining these two genes in one virus, it becomes possible to track the location of transfection while simultaneously evaluating the efficacy of the treatment. As shown in FIG. 13, box I represents human Ad5 sequences, box II represents CMV.HSVtk.polyA.CMV.Luc, and box III represents human Ad5 sequences ΔE3.

The study was conducted by growing JHU-022 tumors on the flanks of nude mice, followed by intratumoral injection with free virus in saline, SELP815K 4 wt % with virus, or SELP47K 4 wt % with virus. Appropriate controls were included. Luciferase expression was measured by injecting luciferin potassium salt intraperitoneally, and following appropriate time to allow distribution of luciferin the animals were imaged using a Xenogen IVIS100 imaging system (Caliper Life Sciences, Hopkinton, Mass.) which allows visualization of luciferase expression without sacrificing the animal. As a measure of efficacy the tumors were measured with calipers every 3 to 4 days. Highly localized gene expression for the virus+SELP815K 4 wt % group was observed, and greatly dispersed gene expression for the virus+saline group. Also there was a notable difference in the transfection levels after three weeks between the groups in the tumors, with the SELP group exhibiting much higher and more consistent transfection levels in the tumors than the virus+saline group. Gene expression in the liver, indicative of significant levels of viral dissemination from the injection site, was present at week three in the virus+saline group. SELP appears to have eliminated this problem in this study.

FIG. 14A shows the changes in tumor size over time for each group from the same study. The experimental groups compared were SELP+virus treatment groups vs. virus+saline with or without GCV, and saline only control. FIG. 14B shows only the two SELP+virus groups compared to free virus with GCV. SELP815K, at 4 wt %, exhibited a 3-fold reduction in tumor size over 33 days compared to virus in saline with no sign of tumor recovery, which was observed at day 21 for virus in saline.

According to these results, at day 33 endpoint of the study, the tumors from the free virus group were, on average, more than three times larger than those in the virus+SELP815K 4 wt % group. Additionally, it appears as if the SELP815K 4 wt %+virus group was still causing a reduction in tumor size, while SELP47K and free virus seem to have some evidence of tumor regrowth. This is a significant outcome as regrowth typically results in full recurrence primarily composed of treatment-resistant cells. It is also important to note that some animals in the SELP815K 4 wt % group showed full recovery, with no evidence of a tumor out to day 33.

In addition to gene transduction and anticancer efficacy we evaluated the safety of SELP hydrogels injected intratumorally without virus in the nude mouse model of human JHU-022 head and neck cancer and followed the animal weight throughout the study duration. As shown in FIG. 15, all animals gained weight throughout the study suggesting no overt toxicity of the treatment system components. We observed no statistical differences in the blood count values, kidney and liver functions, or organ weight at necropsy for SELP injected groups (Table 4), nor were there any histological abnormalities in the heart, liver, kidney, lung and spleen (data not shown). Based on the results in nude mice, the SELP/virus systems were shown to be safe.

TABLE 4

Blood parameters, organ function, and organ weight for tumor bearing nude mice in the SELP/virus efficacy study.

| Blood Parameters | | | Kidney Function | | | Liver Function | | | Organ Weights (mg) | | | | |
|---|---|---|---|---|---|---|---|---|---|---|---|---|---|
| HGB (g/Dl) | WBC (mL$^{-1}$) | PLT (mL$^{-1}$) | CRE (mg/dl) | BUN (mg/dl) | TP (g/dl) | GOT (U/L) | GPT (U/L) | TBil (mg/dl) | Spleen | Kidney | Heart | Liver | Lung |
| 14.76 ± 0.31 | 4.38 ± 0.74 | 336 ± 134.1 | 0.34 ± 0.05 | 29.9 ± 1.4 | 4.98 ± 0.10 | 87 ± 5 | 21 ± 1 | 0.63 ± 0.10 | 104 ± 29 | 198 ± 17 | 131 ± 21 | 1454 ± 141 | 158 ± 57 |
| 13.38 ± 0.15 | 6.25 ± 1.67 | 139.0 ± 7.1 | 0.45 ± 0.15 | 25.2 ± 1.7 | 5.13 ± 0.22 | 73 ± 6 | 31 ± 6 | 0.90 ± 0.14 | 104 ± 52 | 184 ± 21 | 131 ± 6 | 1295 ± 59 | 175 ± 27 |
| 13.30 ± 0.71 | 5.40 ± 1.78 | 187.0 ± 23.9 | 0.30 ± 0.06 | 22.4 ± 1.7 | 4.73 ± 0.41 | 81 ± 13 | 28 ± 8 | 0.95 ± 0.21 | 93 ± 20 | 185 ± 3 | 117 ± 5 | 1404 ± 56 | 114 ± 93 |

Studies have been conducted in vivo in an immunocompetent system to assess the effects of a fully functional immune system on the efficacy and safety of Gene delivery enzyme prodrug therapy mediated by SELP and Ad.HSVtk/GCV. These experiments were performed in a similar manner as the nude mouse model, however the mouse species was changed to CD-1 and cell line was changed to S-180 fibrosarcoma, which is capable of forming subcutaneous solid tumors in immunocompetent mice. The CD-1 mouse strain was used for both i.p. cell propagation and as the host for the subcutaneous tumors. Mice in the cell propagation group were injected intraperitoneally with approximately 6×10$^6$ cells in 0.5 ml of culture media, and weighed. Mouse weight was monitored every other day until mice had gained 15 grams, at which point they were euthanized and cells were drawn from the peritoneum using an 18G needle to avoid cell lysis. Cell solution was adjusted to a concentration of 20×10$^6$/ml in 0.9% normal saline, and 0.1 ml of this solution was injected subcutaneously into both the left and right flanks of separate CD-1 mice. Tumors were seen as early as day 2 post-injection, and allowed to grow to an average size of 7 mm×7 mm before treatment. Once tumors reached the appropriate size, mice were anesthetized and five mice each were intratumorally injected with SELP/Ad.Luc.HSVtk. Following SELP/Ad.Luc.HSVtk injection, mice were injected intraperitoneally with 0.5 ml of 0.65 mg/ml GCV daily for nine days. Tumor size was measured twice per week to assess efficacy as a sign of tumor regression. The results of this study are displayed in FIG. 16. SELP815K(4 wt %)+4.3×10$^9$ PFU of adenovirus was effective in slowing the growth of the tumors. This group is the only group which did not have to be euthanized prematurely due to tumor overgrowth and ulceration.

Safety studies were conducted in immunocompetent mice. In order to examine the ability of SELP to reduce the acute toxicity of the HSV-Tk/GCV system, 4-6 week old female CD-1 immunocompetent mice were injected subcutaneously with the conditions listed in Table 5. Weight was monitored daily for one week and daily injections of 25 mg/kg, intraperitoneal GCV were given to some groups as indicated in Table 5.

TABLE 5

Conditions used for the toxicity study in immunocompetent mice. All conditions were duplicated for the one week and 12 week experiments.

| Condition | N = |
|---|---|
| SELP815K 4% | 4 |
| SELP815K 4% + Ad.HSV-Tk | 4 |
| SELP815K 4% + Ad.HSV-Tk + GCV | 4 |
| Ad.HSV-Tk only | 4 |

TABLE 5-continued

Conditions used for the toxicity study in immunocompetent mice. All conditions were duplicated for the one week and 12 week experiments.

| Condition | N = |
|---|---|
| Ad.HSV-Tk + GCV | 4 |
| Control | 3 |

At the conclusion of the one week study, mice were sacrificed, and blood and organs were collected for analysis. Animal weight gains indicated that there was a trend of acute toxicity in both groups, but there was no statistical significance between the SELP815K 4%+Ad.HSVtk+GCV group and the control condition. These results show that, while SELP does not completely eliminate the toxicity of the GDEPT system, they provide a marked improvement over the free virus condition. It is most likely that this effect is directly related to the improved release characteristics and resulting reduction in systemic distribution and more specifically reduced liver transfection. The results for the immunogenicity portion of the one week study are shown in Table 6. These assessments were performed using a complete blood count. From these results, there is a clear trend pointing to low immunogenicity of the SELP polymer and the adenovirus delivered in SELP, compared to the virus only condition.

TABLE 6

CBC results for the preliminary acute safety study in immunocompetent mice.

| | WBC | LYM | MON | GRA |
|---|---|---|---|---|
| CTRL | 4.63 ± 0.67 | 3.1 ± 0.43 | 0.63 ± 0.13 | 0.9 ± 0.5 |
| SELP815K 4% | 6.3 ± 0.79 | 4.475 ± 0.87 | 0.7 ± 0.27 | 1.125 ± 0.39 |
| Ad.HSVtk + GCV | 8.225 ± 2.51 | 4.325 ± 0.94 | 1.25 ± 0.47 | 2.65 ± 1.32 |
| SELP815K 4% + Ad.HSVtk + GCV | 6.375 ± 3.36 | 3.175 ± 1.33 | 1.025 ± 0.57 | 2.175 ± 1.48 |

The results for the 12 week subchronic toxicity study (FIG. 18) reveal many interesting points about SELP and its ability to improve the Ad.HSVtk/GCV toxicity profile. The results of these statistical analyses are shown in Table 7. These results show that SELP-mediated delivery significantly (p<0.0001) improved the toxicity profile of the Ad.HSV-Tk/GCV compared to virus delivered in saline, to the extent that the systemic toxicity of this system was statistically eliminated (p>0.05 vs. Control). Additionally, SELP was shown to be non-toxic compared to control. The reason for the timing of these observations being later than one week is likely due to the lag time between virus administration and gene expression, in addition to the time required for the metabolized GCV to affect its toxicity systemically. These data suggest that SELP will greatly enhance the efficacy of the HSV-Tk/GCV gene delivery enzyme prodrug therapy system that is known in the art, while reducing toxicity and risk of severe immune response to the administered adenovirus.

TABLE 7

Results of ANOVA and Bonferroni post-test statistical analyses done on data shown in FIG. 18.

| | | | |
|---|---|---|---|
| SELP815K4% + AdV + GCV | Vs AdV + GCV | p < .0001 | Delivery of virus in SELP significantly improves toxicity of the Ad.HSVtk/GCV GDEPT system |
| SELP815K4% + AdV + GCV | Vs Control | p > .05 | Administration of the GDEPT system in SELP eliminates toxicity compared to control |
| SELP815K4% | Vs Control | p > .05 | SELP itself is not toxic in the subchronic period |
| AdV + GCV | Vs Control | p < .0001 | The GDEPT system not controlled by SELP causes significant toxicity |

It is clear that SELP matrices provide an advantage in localizing and prolonging gene expression in HNSCC models in mice. Of the polymer structure and concentrations studied SELP815K hydrogel at 4 wt % concentration resulted in highest enhancement of transfection efficiency in tumor, highest tumor to liver ratio of gene expression, and most effective in decreasing tumor size, setting the stage for choosing this polymer backbone for the proposed competitive renewal period. Coupling these observations with data related to the physicochemical characteristics of the hydrogels described above provides a plausible reason for this observation. The longer elastin units of SELP815K allow maximal release of virus while the longer silk units provide a robust hydrogel even at concentrations as low as 4 wt %.

Example 6: Synthesis of Monomer and Polymer Gene Segments

FIG. 19 illustrates the synthesis of SELP-815K-MMPRS monomer gene segment. The synthesis of the SELP815K-MMPRS monomer gene segment was successfully confirmed by restriction digest with AvaII, which produces a cut within the insert encoding for the GPQGIFGQ sequence (SEQ ID NO: 10), and another 14 base pairs 3' of the BanI site marking the end of the monomer gene, forming a fragment of 311 bp that was visualized by agarose gel electrophoresis. Monomer gene segment generation was additionally confirmed by DNA sequencing.

The synthesis of the polymer gene segment was confirmed by simultaneous double digest with restriction enzymes NcoI and XcmI, which cut 4 base pairs past the 3' end of the polymer gene, and 8 base pairs prior to the 5' end of the polymer gene, respectively. Optimization of ligation conditions revealed that increasing molar ratio combined with increasing total DNA content led to longer polymer gene lengths.

Example 7: Polymer Production and Purification

The small scale protein production capability of pPT317+ SELP815K-MMPRS 6-mer was confirmed by SDS-PAGE. The post-induction samples showed an increased band density corresponding to SELP815K as compared to the pre-induction sample for these colonies, confirming production of SELP815K-MMPRS. It is important to note that in all PAGE gels analyzing SELP that, due to a lack of charged residues, SDS binding to SELP is significantly lower compared to standard proteins. As a consequence SELP regularly appears to be of higher molecular weight than expected on PAGE gels. Large-scale fermentation was performed with a wet cell paste yield of 2.2 kg. Purification of SELP-815K-MMPRS yielded 2.5 grams of material.

Example 8: Polymer Characterization

The newly synthesized SELP815K-MMPRS was initially characterized by MALDI-TOF mass spectrometry, which predicted the molecular weight of SELP815K-MMPRS to be 70,645 Da. While this value does differ from the expected molecular weight of 70,510 Da, this is within reasonable instrument error for proteins of this size.

Amino acid composition analysis confirmed the addition of the expected quantities of amino acids unique to the MMP-responsive insert. Specifically, isoleucine and phenylalanine were not detected in the SELP815K sample, but were detected in approximate quantities of 6 and 7 amino acids respectively in SELP815K-MMPRS, while 14 additional glutamic acid residues were detected in the responsive sequence, approximately equal to expected values for these key indicators (I=6, F=6, Q=12 expected).

SDS-PAGE analysis of enzymatic digestion of these polymers is shown in FIGS. 20-27. It is clear that SELP815K-MMPRS is digested by MMP-2 and MMP-9, and SELP815K without the responsive sequence is not. Additionally, this digestion is dependent on both time of exposure and concentration of MMP.

Example 9: Hydrogel Characterization

Characteristics of hydrogels formed from SELP815K-MMPRS were compared to SELP815K in the context of MMP-sensitivity. Initial analysis consisted of comparing the loss of protein from each hydrogel in the presence and absence of MMPs as an indicator of the sensitivity of the hydrogel to degradation. The degradation and release of total soluble protein from these hydrogels following two weeks of treatment is shown in FIG. 28, while FIGS. 29 and 30 display these results over time for SELP-815K and SELP-815K-MMPRS respectively. SELP815K displayed statistically insignificant levels of increased protein loss in the presence of MMPs, with only minor elevations compared to the control soluble fraction. Exposure of hydrogels composed of SELP815K-MMPRS to MMP-2 and MMP-9 resulted in 63% and 44% higher protein loss compared to control, protein loss from which is attributed to soluble polymer chains which do not participate in crosslinking. As a percentage of total protein in each gel, assuming precise 50 µl gels at 10 wt % would contain 5 mg of polymer, approximately 24% of the polymer per hydrogel was lost as soluble fraction, with enzymatic digestion increasing this percentage to 39% and 35% for MMP-2 and MMP-9-induced degradation, respectively. These results were found to be statistically significant by Tukey's post test of all pairs of values, which revealed a statistical difference between both MMP-2 and MMP-9 and control, and no significance between each other. Results demonstrate that hydrogels composed of SELP815K-MMPRS are degraded by MMP-2 and MMP-9 due to the inclusion of the MMP-responsive sequence GPQGIFGQ.

Characteristics of hydrogels formed from SELP815K-MMPRS were compared to SELP815K in the context of MMP-sensitivity. Initial analysis consisted of comparing the loss of protein from each hydrogel in the presence and absence of MMPs as an indicator of the sensitivity of the hydrogel to degradation. The degradation and release of total soluble protein from these hydrogels following two weeks of treatment is shown in FIG. 28, while FIGS. 29 and 30 display these results over time for SELP-815K and SELP-815K-MMPRS respectively. SELP815K displayed statistically insignificant levels of increased protein loss in the presence of MMPs, with only minor elevations compared to the control soluble fraction. Exposure of hydrogels composed of SELP815K-MMPRS to MMP-2 and MMP-9 resulted in 63% and 44% higher protein loss compared to control, protein loss from which is attributed to soluble polymer chains which do not participate in crosslinking. As a percentage of total protein in each gel, assuming precise 50 µl gels at 10 wt % would contain 5 mg of polymer, approximately 24% of the polymer per hydrogel was lost as soluble fraction, with enzymatic digestion increasing this percentage to 39% and 35% for MMP-2 and MMP-9-induced degradation, respectively. These results were found to be statistically significant by Tukey's post test of all pairs of values, which revealed a statistical difference between both MMP-2 and MMP-9 and control, and no significance between each other. Results demonstrate that hydrogels composed of SELP815K-MMPRS are degraded by MMP-2 and MMP-9 due to the inclusion of the MMP-responsive sequence GPQGIFGQ (SEQ ID NO: 10).

These data show that the polymers used are safe and effective in nude mice and safety in immunocompromised mice as well. Adenoviruses are immunogenic and repeated administration of high doses is needed for therapeutic effect, resulting in adverse effects. The protein polymer design as disclosed herein provide controlled delivery of adenoviruses. The use of these polymers to deliver biomolecule can reduce repeated administration, diminish removal by liver cells and prolong on-target transfection. While specific embodiments are disclosed herein, one of skill in the art will appreciate that this approach is universal and can be used for combination delivery of virus/drug combinations in addition to adenovirus and ganciclovir.

Modifications and improvements of the embodiments specifically disclosed herein are within the scope of the following claims. Without further elaboration, it is believed that one skilled in the area can, using the preceding description, utilize the present disclosure to its fullest extent. Therefore the Examples herein are to be construed as merely illustrative and not a limitation of the scope of the present invention in any way. The embodiments disclosed in which an exclusive property or privilege is claimed are defined as follows.

We claim:

1. A protein polymer, wherein the protein polymer has the structure: [GAGS(GAGAGS)$_2$(GVGVP)$_3$GVGGPQGIF-GQPGKGVP(GVGVP)$_{11}$ (GAGAGS)$_5$GA]$_6$ (SEQ ID NO: 16), and wherein the protein polymer is produced using recombinant methods.

2. A drug delivery system comprising: a. the protein polymer of claim 1; and b. a polynucleotide that encodes an enzyme that converts a prodrug to a therapeutically active compound.

3. A drug delivery system according to claim 2, which comprises a prodrug.

4. A drug delivery system according to claim 2, wherein the prodrug is provided in a solution comprising the protein polymer and the polynucleotide.

5. A drug delivery system according to claim 3 wherein the prodrug is provided separately from the protein polymer and the polynucleotide.

6. A drug delivery system according to claim 2, wherein the polynucleotide comprises an adenovirus.

7. A drug delivery system according to claim 2, wherein the enzyme is thymidine kinase from the Herpes Simplex Virus.

8. A drug delivery system according to claim 2, wherein the prodrug is ganciclovir.

9. A method of delivering an enzyme that converts a prodrug to a therapeutically active compound to a tissue comprising (1) injecting a solution comprising the protein polymer of claim 1 and a polynucleotide that encodes an enzyme that converts a prodrug to a therapeutically active compound into the tissue; and (2) administering the prodrug to the tissue.

* * * * *

SEQUENCE LISTING

```
<160> NUMBER OF SEQ ID NOS: 23

<210> SEQ ID NO 1
<211> LENGTH: 5
<212> TYPE: PRT
<213> ORGANISM: Homo sapiens
<220> FEATURE:
<221> NAME/KEY: VARIANT
<222> LOCATION: (4)..(4)
<220> FEATURE:
<221> NAME/KEY: VARIANT
<222> LOCATION: (4)..(4)
<223> OTHER INFORMATION: Xaa may be any amino acid other than proline

<400> SEQUENCE: 1

Val Pro Gly Xaa Gly
1               5

<210> SEQ ID NO 2
<211> LENGTH: 6
<212> TYPE: PRT
<213> ORGANISM: Bombyx mori

<400> SEQUENCE: 2

Gly Ala Gly Ala Gly Ser
1               5

<210> SEQ ID NO 3
<211> LENGTH: 29
<212> TYPE: PRT
<213> ORGANISM: Nephila clavipes
<220> FEATURE:
<221> NAME/KEY: REPEAT
<222> LOCATION: (26)..(26)
<223> OTHER INFORMATION: There may be multiple Alanines in this position

<400> SEQUENCE: 3

Gly Gln Gly Gly Tyr Gly Gly Leu Gly Gly Gln Gly Ala Gly Arg Gly
1               5                   10                  15
```

Gly Leu Gly Gly Gln Gly Ala Gly Ala Ala Gly Gly Ala
            20                  25

<210> SEQ ID NO 4
<211> LENGTH: 27
<212> TYPE: PRT
<213> ORGANISM: Nephila clavipes
<220> FEATURE:
<221> NAME/KEY: VARIANT
<222> LOCATION: (27)..(27)
<223> OTHER INFORMATION: There may be mulitple Alanines in this position

<400> SEQUENCE: 4

Gly Pro Gly Gly Tyr Gly Pro Gly Gln Gln Gly Pro Gly Gly Tyr Gly
1               5                   10                  15

Pro Gly Gln Gln Gly Pro Ser Gly Pro Ser Ala
            20                  25

<210> SEQ ID NO 5
<211> LENGTH: 5
<212> TYPE: PRT
<213> ORGANISM: Homo sapiens

<400> SEQUENCE: 5

Gly Val Gly Val Pro
1               5

<210> SEQ ID NO 6
<211> LENGTH: 8
<212> TYPE: PRT
<213> ORGANISM: Homo sapiens

<400> SEQUENCE: 6

Ala Pro Gly Gln Ile Ala Gly Gln
1               5

<210> SEQ ID NO 7
<211> LENGTH: 8
<212> TYPE: PRT
<213> ORGANISM: Homo sapiens

<400> SEQUENCE: 7

Gly Pro Gln Gly Leu Ala Gly Gln
1               5

<210> SEQ ID NO 8
<211> LENGTH: 8
<212> TYPE: PRT
<213> ORGANISM: Homo sapiens

<400> SEQUENCE: 8

Gly Pro Leu Gly Ile Ala Gly Ile
1               5

<210> SEQ ID NO 9
<211> LENGTH: 8
<212> TYPE: PRT
<213> ORGANISM: Homo sapiens

<400> SEQUENCE: 9

Ile Pro Glu Asn Phe Phe Gly Val
1               5

<210> SEQ ID NO 10

```
<211> LENGTH: 8
<212> TYPE: PRT
<213> ORGANISM: Homo sapiens

<400> SEQUENCE: 10

Gly Pro Gln Gly Ile Phe Gly Gln
1               5

<210> SEQ ID NO 11
<211> LENGTH: 8
<212> TYPE: PRT
<213> ORGANISM: Homo sapiens

<400> SEQUENCE: 11

Arg Ala Ile His Ile Gln Ala Glu
1               5

<210> SEQ ID NO 12
<211> LENGTH: 8
<212> TYPE: PRT
<213> ORGANISM: Homo sapiens

<400> SEQUENCE: 12

Met Ala Ala Ser Ala Lys Arg Glu
1               5

<210> SEQ ID NO 13
<211> LENGTH: 8
<212> TYPE: PRT
<213> ORGANISM: Homo sapiens

<400> SEQUENCE: 13

Pro Phe Ser Pro Leu Val Ala Thr
1               5

<210> SEQ ID NO 14
<211> LENGTH: 8
<212> TYPE: PRT
<213> ORGANISM: Homo sapiens

<400> SEQUENCE: 14

Gly Pro Leu Gly Ile Ala Gly Gln
1               5

<210> SEQ ID NO 15
<211> LENGTH: 8
<212> TYPE: PRT
<213> ORGANISM: Homo sapiens

<400> SEQUENCE: 15

Gly Pro Gln Ala Ile Ala Gly Gln
1               5

<210> SEQ ID NO 16
<211> LENGTH: 810
<212> TYPE: PRT
<213> ORGANISM: Homo sapiens

<400> SEQUENCE: 16

Gly Ala Gly Ser Gly Ala Gly Ala Gly Ser Gly Ala Gly Ala Gly Ser
1               5                   10                  15

Gly Val Gly Val Pro Gly Val Gly Val Pro Gly Val Gly Val Pro Gly
            20                  25                  30

Val Gly Gly Pro Gln Gly Ile Phe Gly Gln Pro Gly Lys Gly Val Pro
```

```
            35                  40                  45
Gly Val Gly Val Pro Gly Val Gly Val Pro Gly Val Gly Val Pro Gly
 50                  55                  60
Val Gly Val Pro Gly Val Gly Val Pro Gly Val Gly Val Pro Gly Val
 65                  70                  75                  80
Gly Val Pro Gly Val Gly Val Pro Gly Val Gly Val Pro Gly Val Gly
                 85                  90                  95
Val Pro Gly Val Gly Val Pro Gly Ala Gly Ala Gly Ser Gly Ala Gly
                100                 105                 110
Ala Gly Ser Gly Ala Gly Ala Gly Ser Gly Ala Gly Ala Gly Ser Gly
                115                 120                 125
Ala Gly Ala Gly Ser Gly Ala Gly Ala Gly Ser Gly Ala Gly Ala Gly
                130                 135                 140
Ser Gly Ala Gly Ala Gly Ser Gly Val Gly Val Pro Gly Val Gly Val
145                 150                 155                 160
Pro Gly Val Gly Val Pro Gly Val Gly Gly Pro Gln Gly Ile Phe Gly
                165                 170                 175
Gln Pro Gly Lys Gly Val Pro Gly Val Gly Val Pro Gly Val Gly Val
                180                 185                 190
Pro Gly Val Gly Val Pro Gly Val Gly Val Pro Gly Val Gly Val Pro
                195                 200                 205
Gly Val Gly Val Pro Gly Val Gly Val Pro Gly Val Gly Val Pro Gly
                210                 215                 220
Val Gly Val Pro Gly Val Gly Val Pro Gly Val Gly Val Pro Gly Ala
225                 230                 235                 240
Gly Ala Gly Ser Gly Ala Gly Ala Gly Ser Gly Ala Gly Ala Gly Ser
                245                 250                 255
Gly Ala Gly Ala Gly Ser Gly Ala Gly Ala Gly Ser Gly Ala Gly Ala
                260                 265                 270
Gly Ser Gly Ala Gly Ala Gly Ser Gly Ala Gly Ala Gly Ser Gly Val
                275                 280                 285
Gly Val Pro Gly Val Gly Val Pro Gly Val Gly Val Pro Gly Val Gly
                290                 295                 300
Gly Pro Gln Gly Ile Phe Gly Gln Pro Gly Lys Gly Val Pro Gly Val
305                 310                 315                 320
Gly Val Pro Gly Val Gly Val Pro Gly Val Gly Val Pro Gly Val Gly
                325                 330                 335
Val Pro Gly Val Gly Val Pro Gly Val Gly Val Pro Gly Val Gly Val
                340                 345                 350
Pro Gly Val Gly Val Pro Gly Val Gly Val Pro Gly Val Gly Val Pro
                355                 360                 365
Gly Val Gly Val Pro Gly Ala Gly Ala Gly Ser Gly Ala Gly Ala Gly
                370                 375                 380
Ser Gly Ala Gly Ala Gly Ser Gly Ala Gly Ala Gly Ser Gly Ala Gly
385                 390                 395                 400
Ala Gly Ser Gly Ala Gly Ala Gly Ser Gly Ala Gly Ala Gly Ser Gly
                405                 410                 415
Ala Gly Ala Gly Ser Gly Val Gly Val Pro Gly Val Gly Val Pro Gly
                420                 425                 430
Val Gly Val Pro Gly Val Gly Gly Pro Gln Gly Ile Phe Gly Gln Pro
                435                 440                 445
Gly Lys Gly Val Pro Gly Val Gly Val Pro Gly Val Gly Val Pro Gly
                450                 455                 460
```

Val Gly Val Pro Gly Val Gly Val Pro Gly Val Gly Val Pro Gly Val
465                 470                 475                 480

Gly Val Pro Gly Val Gly Val Pro Gly Val Gly Val Pro Gly Val Gly
                485                 490                 495

Val Pro Gly Val Gly Val Pro Gly Val Gly Val Pro Gly Ala Gly Ala
            500                 505                 510

Gly Ser Gly Ala Gly Ala Gly Ser Gly Ala Gly Ala Gly Ser Gly Ala
        515                 520                 525

Gly Ala Gly Ser Gly Ala Gly Ala Gly Ser Gly Ala Gly Ala Gly Ser
    530                 535                 540

Gly Ala Gly Ala Gly Ser Gly Ala Gly Ala Gly Ser Gly Val Gly Val
545                 550                 555                 560

Pro Gly Val Gly Val Pro Gly Val Gly Val Pro Gly Val Gly Gly Pro
                565                 570                 575

Gln Gly Ile Phe Gly Gln Pro Gly Lys Gly Val Pro Gly Val Gly Val
            580                 585                 590

Pro Gly Val Gly Val Pro Gly Val Gly Val Pro Gly Val Gly Val Pro
        595                 600                 605

Gly Val Gly Val Pro Gly Val Gly Val Pro Gly Val Gly Val Pro Gly
    610                 615                 620

Val Gly Val Pro Gly Val Gly Val Pro Gly Val Gly Val Pro Gly Val
625                 630                 635                 640

Gly Val Pro Gly Ala Gly Ala Gly Ser Gly Ala Gly Ala Gly Ser Gly
                645                 650                 655

Ala Gly Ala Gly Ser Gly Ala Gly Ala Gly Ser Gly Ala Gly Ala Gly
            660                 665                 670

Ser Gly Ala Gly Ala Gly Ser Gly Ala Gly Ala Gly Ser Gly Ala Gly
        675                 680                 685

Ala Gly Ser Gly Val Gly Val Pro Gly Val Gly Val Pro Gly Val Gly
    690                 695                 700

Val Pro Gly Val Gly Gly Pro Gln Gly Ile Phe Gly Gln Pro Gly Lys
705                 710                 715                 720

Gly Val Pro Gly Val Gly Val Pro Gly Val Gly Val Pro Gly Val Gly
                725                 730                 735

Val Pro Gly Val Gly Val Pro Gly Val Gly Val Pro Gly Val Gly Val
            740                 745                 750

Pro Gly Val Gly Val Pro Gly Val Gly Val Pro Gly Val Gly Val Pro
        755                 760                 765

Gly Val Gly Val Pro Gly Val Gly Val Pro Gly Ala Gly Ala Gly Ser
    770                 775                 780

Gly Ala Gly Ala Gly Ser Gly Ala Gly Ala Gly Ser Gly Ala Gly Ala
785                 790                 795                 800

Gly Ser Gly Ala Gly Ala Gly Ser Gly Ala
                805                 810

<210> SEQ ID NO 17
<211> LENGTH: 30
<212> TYPE: DNA
<213> ORGANISM: Homo sapiens

<400> SEQUENCE: 17
aggaccgcaa ggaatttttg gacagcctgg                                      30

<210> SEQ ID NO 18

```
<211> LENGTH: 30
<212> TYPE: DNA
<213> ORGANISM: Homo sapiens

<400> SEQUENCE: 18
tccaggctgt ccaaaaattc cttgcggtcc                                          30

<210> SEQ ID NO 19
<211> LENGTH: 602
<212> TYPE: PRT
<213> ORGANISM: artificial sequence
<220> FEATURE:
<223> OTHER INFORMATION: Hybrid of Homo sapein and Bombyx mori

<400> SEQUENCE: 19
```

Met Asp Pro Val Val Leu Gln Arg Arg Asp Trp Glu Asn Pro Gly Val
1               5                   10                  15

Thr Gln Leu Val Arg Leu Ala Ala His Pro Pro Phe Ala Ser Asp Pro
            20                  25                  30

Met Gly Ala Gly Ser Gly Ala Gly Ser Gly Val Gly Val Pro Gly Val
        35                  40                  45

Gly Val Pro Gly Val Gly Val Pro Gly Val Gly Val Pro Gly Lys Gly
    50                  55                  60

Val Pro Gly Val Gly Val Pro Gly Val Gly Val Pro Gly Val Gly Val
65                  70                  75                  80

Pro Gly Ala Gly Ala Gly Ser Gly Ala Gly Ala Gly Ser Gly Ala Gly
                85                  90                  95

Ala Gly Ser Gly Ala Gly Ala Gly Ser Gly Val Gly Val Pro Gly Val
            100                 105                 110

Gly Val Pro Gly Val Gly Val Pro Gly Val Gly Val Pro Gly Lys Gly
        115                 120                 125

Val Pro Gly Val Gly Val Pro Gly Val Gly Val Pro Gly Val Gly Val
    130                 135                 140

Pro Gly Ala Gly Ala Gly Ser Gly Ala Gly Ala Gly Ser Gly Ala Gly
145                 150                 155                 160

Ala Gly Ser Gly Ala Gly Ala Gly Ser Gly Val Gly Val Pro Gly Val
                165                 170                 175

Gly Val Pro Gly Val Gly Val Pro Gly Val Gly Val Pro Gly Lys Gly
            180                 185                 190

Val Pro Gly Val Gly Val Pro Gly Val Gly Val Pro Gly Val Gly Val
        195                 200                 205

Pro Gly Ala Gly Ala Gly Ser Gly Ala Gly Ala Gly Ser Gly Ala Gly
    210                 215                 220

Ala Gly Ser Gly Ala Gly Ala Gly Ser Gly Val Gly Val Pro Gly Val
225                 230                 235                 240

Gly Val Pro Gly Val Gly Val Pro Gly Val Gly Val Pro Gly Lys Gly
                245                 250                 255

Val Pro Gly Val Gly Val Pro Gly Val Gly Val Pro Gly Val Gly Val
            260                 265                 270

Pro Gly Ala Gly Ala Gly Ser Gly Ala Gly Ala Gly Ser Gly Ala Gly
        275                 280                 285

Ala Gly Ser Gly Ala Gly Ala Gly Ser Gly Val Gly Val Pro Gly Val
    290                 295                 300

Gly Val Pro Gly Val Gly Val Pro Gly Val Gly Val Pro Gly Lys Gly
305                 310                 315                 320

Val Pro Gly Val Gly Val Pro Gly Val Gly Val Pro Gly Val Gly Val

-continued

```
                325                 330                 335
Pro Gly Ala Gly Ala Gly Ser Gly Ala Gly Ala Gly Ser Gly Ala Gly
            340                 345                 350
Ala Gly Ser Gly Ala Gly Ala Gly Ser Gly Val Gly Val Pro Gly Val
            355                 360                 365
Gly Val Pro Gly Val Gly Val Pro Gly Val Gly Val Pro Gly Lys Gly
        370                 375                 380
Val Pro Gly Val Gly Val Pro Gly Val Gly Val Pro Gly Val Gly Val
385                 390                 395                 400
Pro Gly Ala Gly Ala Gly Ser Gly Ala Gly Ala Gly Ser Gly Ala Gly
                405                 410                 415
Ala Gly Ser Gly Ala Gly Ala Gly Ser Gly Val Gly Val Pro Gly Val
            420                 425                 430
Gly Val Pro Gly Val Gly Val Pro Gly Val Gly Val Pro Gly Lys Gly
            435                 440                 445
Val Pro Gly Val Gly Val Pro Gly Val Gly Val Pro Gly Val Gly Val
        450                 455                 460
Pro Gly Ala Gly Ala Gly Ser Gly Ala Gly Ala Gly Ser Gly Ala Gly
465                 470                 475                 480
Ala Gly Ser Gly Ala Gly Ala Gly Ser Gly Val Gly Val Pro Gly Val
                485                 490                 495
Gly Val Pro Gly Val Gly Val Pro Gly Val Gly Val Pro Gly Val Gly
            500                 505                 510
Val Pro Gly Val Gly Val Pro Gly Val Gly Val Pro Gly Val Gly Val
        515                 520                 525
Pro Gly Val Gly Val Pro Gly Val Gly Val Pro Gly Val Gly Val Pro
    530                 535                 540
Gly Lys Gly Val Pro Gly Val Gly Val Pro Gly Val Gly Val Pro Gly
545                 550                 555                 560
Val Gly Val Pro Gly Val Gly Val Pro Gly Ala Gly Ala Gly Ser Gly
                565                 570                 575
Ala Gly Ala Gly Ser Gly Ala Gly Ala Met Asp Pro Gly Arg Tyr Gln
            580                 585                 590
Asp Leu Arg Ser His His His His His His
            595                 600

<210> SEQ ID NO 20
<211> LENGTH: 514
<212> TYPE: PRT
<213> ORGANISM: artificial sequence
<220> FEATURE:
<223> OTHER INFORMATION: Hybrid of Homo sapein and Bombyx mori

<400> SEQUENCE: 20

Met Asp Pro Val Val Leu Gln Arg Arg Asp Trp Glu Asn Pro Gly Val
1               5                   10                  15
Thr Gln Leu Val Arg Leu Ala Ala His Pro Pro Phe Ala Ser Asp Pro
            20                  25                  30
Met Gly Ala Gly Ser Gly Ala Gly Ser Gly Val Gly Val Pro Gly Val
        35                  40                  45
Gly Val Pro Gly Val Gly Val Pro Gly Val Gly Val Pro Gly Lys Gly
    50                  55                  60
Val Pro Gly Val Gly Val Pro Gly Val Gly Val Pro Gly Val Gly Val
65                  70                  75                  80
Pro Gly Ala Gly Ala Ser Gly Ala Gly Ala Ser Gly Ala Gly Ala Ser
```

```
                        85                  90                  95
Gly Ala Gly Ala Ser Gly Val Gly Val Pro Gly Val Gly Val Pro Gly
                100                 105                 110
Val Gly Val Pro Gly Val Gly Val Pro Gly Lys Gly Val Pro Gly Val
                115                 120                 125
Gly Val Pro Gly Val Gly Val Pro Gly Val Gly Val Pro Gly Ala Gly
            130                 135                 140
Ala Ser Gly Ala Gly Ala Ser Gly Ala Gly Ala Ser Gly Ala Gly Ala
145                 150                 155                 160
Ser Gly Val Gly Val Pro Gly Val Gly Val Pro Gly Val Gly Val Pro
                165                 170                 175
Gly Val Gly Val Pro Gly Lys Gly Val Pro Gly Val Gly Val Pro Gly
                180                 185                 190
Val Gly Val Pro Gly Val Gly Val Pro Gly Ala Gly Ala Ser Gly Ala
                195                 200                 205
Gly Ala Ser Gly Ala Gly Ala Ser Gly Ala Gly Ala Ser Gly Val Gly
            210                 215                 220
Val Pro Gly Val Gly Val Pro Gly Val Gly Val Pro Gly Val Gly Val
225                 230                 235                 240
Pro Gly Lys Gly Val Pro Gly Val Gly Val Pro Gly Val Gly Val Pro
                245                 250                 255
Gly Val Gly Val Pro Gly Ala Gly Ala Ser Gly Ala Gly Ala Ser Gly
                260                 265                 270
Ala Gly Ala Ser Gly Ala Gly Ala Ser Gly Val Gly Val Pro Gly Val
            275                 280                 285
Gly Val Pro Gly Val Gly Val Pro Gly Val Gly Val Pro Gly Lys Gly
            290                 295                 300
Val Pro Gly Val Gly Val Pro Gly Val Gly Val Pro Gly Val Gly Val
305                 310                 315                 320
Pro Gly Ala Gly Ala Ser Gly Ala Gly Ala Ser Gly Ala Gly Ala Ser
                325                 330                 335
Gly Ala Gly Ala Ser Gly Val Gly Val Pro Gly Val Gly Val Pro Gly
            340                 345                 350
Val Gly Val Pro Gly Val Gly Val Pro Gly Lys Gly Val Pro Gly Val
            355                 360                 365
Gly Val Pro Gly Val Gly Val Pro Gly Val Gly Val Pro Gly Ala Gly
            370                 375                 380
Ala Ser Gly Ala Gly Ala Ser Gly Ala Gly Ala Ser Gly Ala Gly Ala
385                 390                 395                 400
Ser Gly Val Gly Val Pro Gly Val Gly Val Pro Gly Val Gly Val Pro
                405                 410                 415
Gly Val Gly Val Pro Gly Val Gly Val Pro Gly Val Gly Val Pro Gly
                420                 425                 430
Val Gly Val Pro Gly Val Gly Val Pro Gly Val Gly Val Pro Gly Val
                435                 440                 445
Gly Val Pro Gly Val Gly Val Pro Gly Lys Gly Val Pro Gly Val Gly
            450                 455                 460
Val Pro Gly Val Gly Val Pro Gly Val Gly Val Pro Gly Val Gly Val
465                 470                 475                 480
Pro Gly Ala Gly Ala Gly Ser Gly Ala Gly Ala Gly Ser Gly Ala Gly
                485                 490                 495
Ala Met Asp Pro Gly Arg Tyr Gln Asp Leu Arg Ser His His His His
            500                 505                 510
```

His His

<210> SEQ ID NO 21
<211> LENGTH: 830
<212> TYPE: PRT
<213> ORGANISM: artificial sequence
<220> FEATURE:
<223> OTHER INFORMATION: Hybrid of Homo sapein and Bombyx mori

<400> SEQUENCE: 21

```
Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala Gly Ser Gly Ala Gly Ala Gly Ser Gly Ala Gly Ala Gly
        35                  40                  45

Ser Gly Val Gly Val Pro Gly Val Gly Val Pro Gly Val Gly Val Pro
    50                  55                  60

Gly Val Gly Val Pro Gly Lys Gly Val Pro Gly Val Gly Val Pro Gly
65                  70                  75                  80

Val Gly Val Pro Gly Val Gly Val Pro Gly Val Gly Val Pro Gly Val
                85                  90                  95

Gly Val Pro Gly Val Gly Val Pro Gly Val Gly Val Pro Gly Val Gly
            100                 105                 110

Val Pro Gly Val Gly Val Pro Gly Val Gly Val Pro Gly Val Gly Val
        115                 120                 125

Pro Gly Ala Gly Ala Gly Ser Gly Ala Gly Ala Gly Ser Gly Ala Gly
130                 135                 140

Ala Gly Ser Gly Ala Gly Ala Gly Ser Gly Ala Gly Ala Gly Ser Gly
145                 150                 155                 160

Ala Gly Ala Gly Ala Gly Ser Gly Ala Gly Ala Gly Ser Gly Ala Gly
                165                 170                 175

Ala Gly Ser Gly Val Gly Val Pro Gly Val Gly Val Pro Gly Val Gly
            180                 185                 190

Val Pro Gly Val Gly Val Pro Gly Lys Gly Val Pro Gly Val Gly Val
        195                 200                 205

Pro Gly Val Gly Val Pro Gly Val Gly Val Pro Gly Val Gly Val Pro
210                 215                 220

Gly Val Gly Val Pro Gly Val Gly Val Pro Gly Val Gly Val Pro Gly
225                 230                 235                 240

Val Gly Val Pro Gly Val Gly Val Pro Gly Val Gly Val Pro Gly Val
                245                 250                 255

Gly Val Pro Gly Ala Gly Ala Gly Ser Gly Ala Gly Ala Gly Ser Gly
            260                 265                 270

Ala Gly Ala Gly Ser Gly Ala Gly Ala Gly Ser Gly Ala Gly Ala Gly
        275                 280                 285

Ser Gly Ala Gly Ala Gly Ala Gly Ser Gly Ala Gly Ala Gly Ser Gly
    290                 295                 300

Ala Gly Ala Gly Ser Gly Val Gly Val Pro Gly Val Gly Val Pro Gly
305                 310                 315                 320

Val Gly Val Pro Gly Val Gly Val Pro Gly Lys Gly Val Pro Gly Val
                325                 330                 335

Gly Val Pro Gly Val Gly Val Pro Gly Val Gly Val Pro Gly Val Gly
            340                 345                 350
```

```
Val Pro Gly Val Gly Val Pro Gly Val Gly Val Pro Gly Val Gly Val
        355                 360                 365

Pro Gly Val Gly Val Pro Gly Val Gly Val Pro Gly Val Gly Val Pro
        370                 375                 380

Gly Val Gly Val Pro Gly Ala Gly Ala Gly Ser Gly Ala Gly Ala Gly
385                 390                 395                 400

Ser Gly Ala Gly Ala Gly Ser Gly Ala Gly Ala Gly Ser Gly Ala Gly
        405                 410                 415

Ala Gly Ser Gly Ala Gly Ala Gly Ser Gly Ala Gly Ala Gly
        420                 425                 430

Ser Gly Ala Gly Ala Gly Ser Gly Val Gly Val Pro Gly Val Gly Val
        435                 440                 445

Pro Gly Val Gly Val Pro Gly Val Gly Val Pro Gly Lys Gly Val Pro
        450                 455                 460

Gly Val Gly Val Pro Gly Val Gly Val Pro Gly Val Gly Val Pro Gly
465                 470                 475                 480

Val Gly Val Pro Gly Val Gly Val Pro Gly Val Gly Val Pro Gly Val
        485                 490                 495

Gly Val Pro Gly Val Gly Val Pro Gly Val Gly Val Pro Gly Val Gly
        500                 505                 510

Val Pro Gly Val Gly Val Pro Gly Ala Gly Ala Gly Ser Gly Ala Gly
        515                 520                 525

Ala Gly Ser Gly Ala Gly Ala Gly Ser Gly Ala Gly Ala Gly Ser Gly
        530                 535                 540

Ala Gly Ala Gly Ser Gly Ala Gly Ala Gly Ser Gly Ala Gly Ala Gly
545                 550                 555                 560

Ala Gly Ser Gly Ala Gly Ala Gly Ser Gly Val Gly Val Pro Gly Val
        565                 570                 575

Gly Val Pro Gly Val Gly Val Pro Gly Val Gly Val Pro Gly Lys Gly
        580                 585                 590

Val Pro Gly Val Gly Val Pro Gly Val Gly Val Pro Gly Val Gly Val
        595                 600                 605

Pro Gly Val Gly Val Pro Gly Val Gly Val Pro Gly Val Gly Val Pro
        610                 615                 620

Gly Val Gly Val Pro Gly Val Gly Val Pro Gly Val Gly Val Pro Gly
625                 630                 635                 640

Val Gly Val Pro Gly Val Gly Val Pro Gly Ala Gly Ala Gly Ser Gly
        645                 650                 655

Ala Gly Ala Gly Ser Gly Ala Gly Ala Gly Ser Gly Ala Gly Ala Gly
        660                 665                 670

Ser Gly Ala Gly Ala Gly Ser Gly Ala Gly Ala Gly Ala Gly Ser Gly
        675                 680                 685

Ala Gly Ala Gly Ser Gly Ala Gly Ala Gly Ser Gly Val Gly Val Pro
        690                 695                 700

Gly Val Gly Val Pro Gly Val Gly Val Pro Gly Val Gly Val Pro Gly
705                 710                 715                 720

Lys Gly Val Pro Gly Val Gly Val Pro Gly Val Gly Val Pro Gly Val
        725                 730                 735

Gly Val Pro Gly Val Gly Val Pro Gly Val Gly Val Pro Gly Val Gly
        740                 745                 750

Val Pro Gly Val Gly Val Pro Gly Val Gly Val Pro Gly Val Gly Val
        755                 760                 765

Pro Gly Val Gly Val Pro Gly Val Gly Val Pro Gly Ala Gly Ala Gly
```

```
                770                 775                 780
Ser Gly Ala Gly Ala Gly Ser Gly Ala Gly Ala Gly Ser Gly Ala Gly
785                 790                 795                 800

Ala Gly Ser Gly Ala Gly Ala Gly Ser Gly Ala Gly Ala Met Asp Pro
                805                 810                 815

Gly Arg Tyr Gln Asp Leu Arg Ser His His His His His
                820                 825                 830

<210> SEQ ID NO 22
<211> LENGTH: 390
<212> TYPE: DNA
<213> ORGANISM: artificial sequence
<220> FEATURE:
<223> OTHER INFORMATION: Hybrid of Homo sapein and Bombyx mori

<400> SEQUENCE: 22
ggcacccgct ccgcttcctg ctccagcacc tgagccagcg cctgcgccgg atcctgcgcc      60
cgcgccagag cccgcgcctg cgccgctacc agcacccgct cccgggacgc caactccagg     120
aactcctaca cccggcactc ctactcccgg tacgcctact cctggtacgc caactccagg     180
aactcctaca cccggcactc ctactcccgg tacgcctact cctggtacgc ctacacctgg     240
tactccaacg cccggcacac ctaccccggg aacacctttt ccaggtacac caactcccgg     300
aacgcctaca cccggaacac cgacacctgg cactccaaca ccagagcccg cgccagctcc     360
agaaccggct cctgcaccgc tgccggcacc                                      390

<210> SEQ ID NO 23
<211> LENGTH: 5
<212> TYPE: PRT
<213> ORGANISM: Homo sapiens

<400> SEQUENCE: 23

Gly Lys Gly Val Pro
1               5
```